(12) United States Patent
Visser et al.

(10) Patent No.: US 7,022,836 B2
(45) Date of Patent: *Apr. 4, 2006

(54) METHODS FOR PRODUCING AND TRANSFORMING CASSAVA PROTOPLASTS

(75) Inventors: Richard G. F. Visser, ET Bennekom (NL); Christiaan J. J. Raemakers, CN Amhem (NL); Evert Jacobson, BD Wageningen (NL); Johanna Elizabeth M. Bergorvoet van Deelen, JM Renkum (NL)

(73) Assignee: National Starch and Chemical Investment Holding Corporation, New Castle, DE (US)

(*) Notice: Subject to any disclaimer, the term of this patent is extended or adjusted under 35 U.S.C. 154(b) by 186 days.

This patent is subject to a terminal disclaimer.

(21) Appl. No.: 10/119,226

(22) Filed: Apr. 9, 2002

(65) Prior Publication Data

US 2003/0124724 A1 Jul. 3, 2003

Related U.S. Application Data

(63) Continuation-in-part of application No. 09/832,626, filed on Apr. 11, 2001, which is a continuation-in-part of application No. 09/180,481, filed on Feb. 1, 1999, now Pat. No. 6,551,827.

(51) Int. Cl.
*C08B 31/00* (2006.01)
*C08B 33/00* (2006.01)
*C08B 35/00* (2006.01)

(52) U.S. Cl. .......................... 536/45; 536/47; 536/48; 536/49; 536/50

(58) Field of Classification Search ............... 514/60; 536/45

See application file for complete search history.

(56) References Cited

U.S. PATENT DOCUMENTS

| | | | |
|---|---|---|---|
| 3,029,168 A | | 4/1962 | Meisel et al. |
| 5,275,837 A | * | 1/1994 | Eastman ...................... 426/661 |
| 5,665,786 A | * | 9/1997 | Xu et al. ..................... 521/84.1 |
| 5,824,798 A | | 10/1998 | Tallberg et al. |

FOREIGN PATENT DOCUMENTS

| | | |
|---|---|---|
| EP | 1 314 742 | 5/2003 |
| EP | 1 314 743 | 5/2003 |
| WO | WO 97/44473 | 11/1997 |
| WO | WO 00/54606 | 9/2000 |

OTHER PUBLICATIONS

Banks et al., "Physiochemical Studies on Starches, Part 63, The Molecular Size and Shape of Amylopectin", die starke, vol. 24, No. 8, pp. 245-251, 1972.

STARCH, 2nd ed., Chapter XIII, "Tapioca, Arrowroot, and Sago Starches: Production" by Douglas Corbishley and William Miller, 1984.

Munyika et al., "Cassava starch biosynthesis: new avenues for modifying starch quantity and quality", Euphytica 96: 65-75, 1997.

Munyika et al, "Pinpointing towards improved transformation and regeneration of cassava (Manihot esculenta Crantz)", Plant Science 135: 87-101, 1998.

Raemakers et al., "Regeneration and transformation of cassava", Euphytica 96: 153-161, 1997.

Raemakers et al., "Production of Amylose-Free Cassava Plants by Genetic Modification", Fifth International Scientific Meeting of the Cassava Biotechnology Network, Nov. 4-9, 2001, p. S3-13.

Raemakers et al., "Analysis of genetically modified cassava plants", Powerpoint presentation relating to the presentation of Abstract S3-13 CBNV Meeting (see above) Nov. 4-9, 2001.

Salehuzzaman et al., "Isolation and characterization of a cDNA encoding granule-bound starch synthase in cassava (Manihot esculenta Crantz) and its antisense expression in potato", Plant Molecular Biology 23: 947-962, 1993.

Peng Zhang, "Studies of cassava (Manihot esculenta Crantz) transformation towards genetic improvement", Dissertation submitted to the Swiss Federal Institute of Technology Zurich, Diss. ETH No. 13962, Dec. 2000.

(Continued)

*Primary Examiner*—James O. Wilson
*Assistant Examiner*—Traviss C. McIntosh, III
(74) *Attorney, Agent, or Firm*—Karen G. Kaiser

(57) ABSTRACT

The invention relates to a method for producing protoplasts of cassava or closely related species, which protoplasts are capable of regeneration into plants. The method comprises producing friable embryogenic callus from explants of cassava or closely related species and isolating protoplasts from said friable embryogenic callus. The invention also concerns protoplasts obtainable by said method. The invention further relates to a method for transforming such a protoplast of cassava or closely related species, and transformed protoplasts obtainable thereby. In addition, the invention concerns a method for regenerating plants from these protoplasts and a cassava plant or closely related species obtainable thereby.

Starch isolated from tubers of such cassava plants have an increased amylopectin content. The starch and a method for isolating it from said plants also forms part of the invention.

10 Claims, 5 Drawing Sheets

OTHER PUBLICATIONS

Carvalho et al., "Isolation and characterization of cassava (Manihot esculenta Crantz) clone with novel", Plant Biology 2000, Abs #261.

Anonymous, 1985. CIAT: Annual report: Centro International de Agricultura Tropical, Cali, Columbia, pp. 197-217.

Anthony, P., Davey, M.R., Power, J.B., Lowe, K.C. 1995. An Improved Protocol for the Culture of Cassava Leaf Protoplasts. Plant Cell Tissue and Organ Culture; 4229-302.

Buiteveld, J.; Creemers-Molenaar, J.; 1994. Plant Regeneration from protoplasts Isolated from Suspension Cultures of Leek . . . Plant Science. 100:203-210.

Cao, J., Duan, X., McElroy, D., Wu, R. 1990. Regeneration of Herbicide Resistant Transgenic Rice Plants Following Microprojectile-Mediated . . . Plant Cell Rep. 9:611:614.

Chang, Y.F., Wang, W.C., Colleen, Y.W., Nguyen, H.T. and Wong, Jr. 1991. Plant Regeneration From Protoplasts Isolated From Long-Term Cell . . . Plant Cell Rep. 9:611-614.

Chen, W.H., Davey,, MR., Power, J.B., and Cocking, E.C. 1988. Sugarcane Protoplasts: Factors Affecting Division and Plant . . . Plant Cell Rep. 7:344-347.

Chen, W.H., Gartland, K.M.A., Davey, MR., Sotak, R., et al. 1987. Transformation of Sugarcane Protoplasts by Direct Uptake of a . . . Plant Cell Rep. 6:297-301.

Delaat, A., and Blaas, J., 1987. An imrpoved Method for Protoplast Microinjection Suitable for Transfer of Entire Plant Chromosoes. Plant Sci. 50:161-169.

Fitch, M.M.M., Pang, S.Z. et al. 1994. Genetic Transformation in Carica Papaya . . . In: Bajai (Eds.) Biotechnology in Agri. and Forestry vol. 29, p. 237-255.

Dons, J.J.M., and Bouwer, R. 1986. Improving the Culture of Cucumber Protoplasts . . . Proceeding of an International Symposium on Nuclear . . . Aug. 19-23, 1985. P 498-504.

Fraley, R.T., Rogers, S.G., and Horsch, R.B. 1986. Genetic transformation in higher plants. CRC Critical Reviews in Plant Sciences 4(1):1-46.

Gordon-Kamm, W.J., Spencer, TM, Mangano, M.R., Adams, T.R., et al., 1990. Transformation of Maize Cells and Regeneration of Fertile Transgenic . . . The Plant Cell. 2:603-618.

Gresshoff, P.M., and Doy, C.H. 1974. Development and Differentiation of Haploid Lycopersico Esculentum (tomato). Planta 107:161-170.

Griesbach, R.J., and Hammond, . 1993. Incorporation of the GUS gene into Orchids Via Embryo Electrophoresis. Acta. Hort. 336:165-169.

Guerineau F. & Mullineaux P.M. 1993. Plant Transformation and . . . In: Croy R.R.D. (ed.), Plant Mol. Biol. Labfax, BIO. S Scientific Publishers, Oxford UK 1993, p. 121-148.

Horn, M.E., Shillito, R.D., Conger, B.V., and Harms, C.T. 1988. Transgenic Plants of, Orchardgrass (Dactylls Glomerta L.) from Protoplasts. Plant Cell Rep. 7:469-472.

Hovenkamp-Hermelink, JHM, Devries JN, Admase P., Jacobsen, E., Withold B., Feenstra WJ, 1988. Rapid Estimation of the Amylose/Amylopectine . . . Potato Res. 31:241-246.

Jones H., Tempelaar M.J., and Jones, M.G.K. 1987. Recent Advances in Plant Electroporation. Oxford Surveys of Plant Mol. and Cell Biol. 4:347-357.

Kaepper, H.F., Gu, W., Somres, D.A., Rines,H.W., Cockburn, A.F. 1990. Silicon Carbide Fiber-Mediated DNA Delivery into Plant Cells. Plant Cell Rep. 8:415-418.

Klein T.M., Kornstein, L., Sanfords J.C., and Fromm M.E. 1989. Genetic Transformation of Maize Cells by Particle Bombardment. Plant Physiol. 91:440-444.

Konan, N.K., et al. Target Tissue for Shoot Production and Genetic Transformation in . . . Second Intl'. Scien.Meeting of Cassava Biotechnology Network 11. Bogor IN. 276-288. 1994.

Kyozuka, J., Otoo; E., and Shimamoto, K. 1988. Plant Regeneration from Protoplasts of Indica Rice: Genotypic Differences in Culture Respond. Theor. Appl. Genet 76:887-890.

Lorz, H., Baker, B., and Schell, J. 1985. Gene Transfer to Cereal Cells Mediated by Protoplast Transformation. Mol. Gen. Genetic 199:178-182.

Luong, H.T., Shewry, P.R., and Lazzeri, P.A.1994. Gene Transfer to Cassava Somatic Embryose . . . In: Second Intl. Scien. Meet. of Cassava Biotech. Network 11 Bogor, IN 303-314.

Mathews, H. Carcamo, R., Chavarriaga, Schopke, C.P., Fauquet, C., et al. 1993. Improvement of Somatic Embryogenesis and Plant Recovery in Cassava. Plant Cell Rep. 12:328-333.

Mroginski and Socchi, 1992. Somatic Embryogenesis of . . . In: Roca, W.M., and Thro, A.M. (Eds.). Proceed. First Scient. Meet. of the Cassava . . . Cartagena CO 25-28 p. 175-179.

Mukherjee, A. 1994 Embryogenesis and Regeneration from Cassava Galli of . . . The Cassava Bio. Network. Proceed. Second Intl. Scient. Meet. bogor, IN , 22-26 p. 375-387.

Murashige, T., and Skoog, F. 1962. A Revised Medium for Rapid Growth and Bioassay with Tobacco Cultures. Physiol. Plantarum 15 473-497.

Nakano, M, Hoshino, Y., and Mil, M. 1994. Regeneration of Transgenic Plants of Grapevine (Vitis Vinifera L.) via . . . J. of Exp. Bot. 45 (274): 649-656.

Narayanaswamy, T.C., et al. 1995. Somatic Embryogenesis and Plant . . . The Cassava Biot. Network. Proceeding of Second Intl. Scientific Meet. Bogor, IN. 22-26 1994. p. 324-335.

Thottappilly G., Monti, L et al (eds.), NG SYS (1992) Tissue Culture of Root and Tuber . . . at IITA. In: Biot.: Enhancing Research on Tropical . . . IITQ, Ibadan, Nigeria 135-141.

Nzoghe, D., 1989. Recherche de Conditions Permettant . . . Extension a la Culture de Protoplastes. These. Univ. De Paris Sud Centre D'Orsay. p 119.

Ow, D.W., Wood, K.V., Deluca, M., et al. 1986. Transient and Stable Expression of the Firefly Luciferse Gene in Plant Cells . . . science 234:856-859.

Potrykus, I Saul, M., Paskowski, J. and Shillito, R.D. 1985. Direct Gene Transfer into Protoplasts of a Graminacious Monocot. Mol. Gen. Genet. 199:183-188.

Power, J.B., Bery, S.F., Chapman,J.V., and Cocking, E.C. 1979. Somatic Hybrids Between Unilateral Cross-Incompatible Petunia Species. Theor. Appl. Genet. 55:97-99.

Raemakers, C.J.J.M. 1993. Primary and Cyclic Somatic Embryogenesis in . . . Manihot esculenta Crantz. PhD theiss Agri. Univ. Wageningen, The Netherlands, p119.

Raemakers, C.J.J.M., Bessembinder, J., Staritsky, G. et al., 1993a. Induction, Germination and Shoot Development of Somatic Embryos in . . . Plant Cell Tissue . . . 33:151-156.

Raemakers, C.J.J.M., Amati, M., Staritsky,G., Jacobsen, E., and Visser, R.G.F., 1993b. Cyclic Somatic Embryogenesis and Plant Regeneration in . . . Annals of Bot. 71:289-294.

Raemakers, C.J.J.M., Schavemaker,CM., Jacobsen, E., and Visser, R.G.F., 1993c. Improvements of Cyclic Somatic Embryogenesis of . . . Plant Cell Rep. 12:226-229.

Raemakers, K., et al. 2000,Towards a Routine Transformation . . . In: Carvalho, L.J.C.B., Thro, A.M. and Vilarinhos A.D. (eds). Cassava Biot. IV Intl. Scien. Meet.-CBN, p250-267.

Raemakers, K., Schreuder, M., Pereira, I., Muniykwa, T., Jacobsen, E., and Visser, R., 2001. Progress Made in FEC Transformation of Cassava. Euphytica (in press).

Rhodes, C.A., Pierce, D.A., Metler, I.J., Mascarenhas, D., and Detmer, J.J. 1988. Genetically transformed maize plants Erom Protoplasts. Science 240:204-207.

Salehuzzaman S.N.I.M., Jacobsen, E. and RGF Visser, 1993. Isolation and Characterization of a CDNA Encoding Granula-bound . . . ,Plant Mol. Biio. 23:947-962.

Salehuzzaman S.N.I.M., Jacobsen, E. and RGF Visser, 1994. Expression patterns of two starch biosynthetic genes in in vitro cultured cassava plants . . . 98:53-62.

Schenk, R.U. & Hildebrandt, A.C. 1972. Medium and techniques for induction and growth of monocotyledonous and dicotyledonous . . . Canadian Journal of Botany 50:199-204.

Schreuder, M.M., Raemakers, C.J.J.M., Jacobsen, E. & Visser, R.G.F. 2001. Efficient Production of Transgenic Plants by Agrobacterium-Mediated . . . Euphytica (in press).

Scorza, R., Cordts, J.M.,Ramming, D.W., and Emershad,R.I. 1995. Transformation of Grape (Vitis Viifera L.) Zygotic-Derived Somatic Embryos . . . Plant Cell Rep 14:589-592.

Shahin, E.A., and Shepard, J.F. 1980. Cassava Mesophll Protoplasts: Isolation, Proliferation and Shoot Formation. Plant Science Letters 17:459-465.

Shimamoto, K. Terada, R., Izawa, T., and Fujimoto, H. 1989. Fertile Transgenic Rite Plants Regenerated from Transformed Protoplasts. Nature 338:274-276.

Sofiari, E. 1996. Regeneration and Transformation in Cassava Manihot Esculenta Crantz, PhD Thesis Agri Univ. Wageningen, The Netherlands. p136.

Songstad, D.D., Somers, D.A., and Griesbach, R.J. 1995. Advances in Alternative DNA Delivery Techniques. Plant Cell Tissue and Organ Culture 40:1-15.

Stamp, J.A., and Henshaw, G.G. 1987A. Somatic Embryogenesis from Clonal Leaf Tissue of Cassava. Annals of Bot. 59:445-450.

Stamp, J.A. 1987. Somatic Embryogenesis in Cassava: The Anatomy and morphology of the Regeneration process. Annals of Bot. 59:451-459.

Stamp, J.A. and Henshaw, G.G. 1987Bb. Secondary Somatic Embryogenesis and Plant Regeneration in Cassava. Plant Cell Tissue and Organ Culture 10:227-233.

Stamp, J.A., and Henshaw, G.G. 1982. Somatic Embryogenesis in Cassava. Zeitschrift fur Pflanzenphysiologie. 105:183-187.

Sudarmonowati and Bachtiar, 1995. Induction of Somatic Embryogenesis . . . The Cassava Biot. Network. Proceeding of the Second Intl. Scien. Meet. Bogar, IN 22-26 1994 p 364-374.

Sudarmonowati, E., and G.G. Henshaw. 1992. The Induction of Somatic Embryogenesis of Recalcitrant . . . In: Roca, W.M., and Thro., A.M. (Eds) Proceed. Aug. 25-28, 1992 p. 128-133.

Suhandano, S., Hughes, J., Brown, K., Sirju-Charan, G., Hughes, M. 2000. Characterization of an elongation facto-1-alpha . . . Cassava Bio. IV Intl. Scien. Meet-CBN, p572-581.

Szabados L., Hayos, R. and Roca W. 1987. In Vitro Somatic Embryogenesis and Plant Regeneration of Cassava. Plant Cell Rep. 6:248-251.

Taylor, N.J., Clarke, M. et al. 1992. The Induction of Somatic Embryogenesis in Fifteen African Cassava cultivars . . . Cartagena, CO Aug. 25-28, 1992 p. 134-137.

Taylor, N.J., Edwards, et al. 1995. Producton of Friable Embryogenic Calli and . . . Second Intl. Scient. Meet . . . Bogor, IN p. 229-240.

Taylor, N.J., Masona, M.V., et al 2000. Production of Genetically Modified Plants . . . In: Carvalho, L. J. et al. Cassava Biot. IV Intl . . . p. 267-276.

Thompson, J.C., Movva, N.R., Tizard, R. et al. 1987. Characterization of the Herbicide-Resistance Gene bar from Streptomyces hygroscopius. The EMBO J.6 (9): 2519-2523.

Toriyama, K., Arimoto, Y., et al. 1988. Transgenic Rice Plants After Direct Gene Transfer into Protoplasts. Bio/Technology 6:1072-1074.

Thro, AMT, Fregene, M. et al. 1999. Genetic Biot. and Cassava Development. IN: Hohn, T. and Leisinger, K.M. (eds.) Biotechnology of food crops in developing . . . p. 141-185.

Visser, RGF, Hergersberg, M. van der Ley, FR et al., 1989. Molecular Cloning and Partial Characterization of the Gene for Granula-Bound . . . Plant Science 64:185-192.

Visser, RGF, Stolte, A., Jacobsen, E., 1991. Expression of a Chiemeric Granulation-Bound Starch Synthase-GUS Gene in Transgenic Potato Tubers. Plant Molec. Bio. 17:691-699.

Walker, P.M.B. 1989. Chambers Biology Dictionary. W&R Chamber Ltd. Clay Ltd., St. Ives Plc. England. p. 205.

Wolters, A.M.A, Schoenmakers, H.C.H., et al., 1991. Limited DNA elimination from the Irradiated Potato Parent in Fushion Produdts of Albino . . . Theor. Appl. Genet. 83:225-232.

Wordragen, M.F., and Dons, Hinl 1992. Agrobacterium tumefaciens Mediated Transformation of Recalcitrant Crops. Plant Mol. Biol. Reporter 10:12-36.

Woodward, B., and Puonti Kaerlas, 2001. Somatic Embryogenesis from Floral Tissues of Cassava (Manihot Esculenta Crantz. Euphytica (in press).

* cited by examiner pH 3.0, 5% Solids

US 7,022,836 B2

METHODS FOR PRODUCING AND TRANSFORMING CASSAVA PROTOPLASTS

This is a Continuation-in-part of application U.S. Ser. No. 09/832,626 filed Apr. 11, 2001 which is a Continuation-in-part of application U.S. Ser. No. 09/180,481 filed Feb. 1, 1999, which was patented as U.S. Pat. No. 6,551,827 on Apr. 22, 2003, the contents of which are incorporated herein by reference.

BACKGROUND OF THE INVENTION

Genetic modification or transformation is the technique wherein one or a few gene(s) are added to a commercially interesting genotype or clone. In principle a successful transformation system requires an efficient system where new plants are formed from specific plant parts (stem, leaf, node and so on) or from specific tissue (somatic embryos, embryogenic callus, friable embryogenic callus) induced on specific plant parts or from protoplasts (single cells without cell wall) derived of these parts or from the specific tissue, a system to transfer DNA molecules to the plant's parts or protoplasts and a system to select tissue and plants which contain and express the introduced gene(s). In principle protoplasts are the most ideal system for DNA delivery. They can be cultured as single cells that produce multicellular colonies from which plants develop. Plants derived from protoplasts are generally clonal in origin. This provides a useful tool for any transformation system, because it will eliminate chimerism in transgenic plants.

Cassava is very recalcitrant for plant regeneration of protoplasts. There is only one report of shoot regeneration from protoplasts of cassava (Shahin and Shephard, 1980). They used well expanded leaves for the isolation of protoplasts. Despite considerable efforts, plant regeneration from protoplasts (isolated from leaves, sterns, and roots) has never been repeated since then (Anonymous, 1985; Nzoghe, 1991; Anthony et al., 1995, Sofiari, 1996). A logical approach was to use tissues which contain embryogenic cells. Such cells are found in the apical meristems, young leaves or somatic embryos cultured on auxin supplemented media (Stamp and Henshaw, 1987a; Raemakers et al., 1993a). However, protoplasts isolated from these tissues gave in the best case green callus and adventitious roots (Sofiari, 1996). Recently, a new type of somatic embryogenesis was developed. In this in vitro system the embryos do not develop beyond the (pre-)globular stage and the embryogenic callus is highly friable (Taylor et al., 1995). Transfer of this friable embryogenic callus (FEC) to liquid medium resulted in a suspension-like culture. In leek (Buitenveld and Creemers, 1994), petunia (Power et al., 1979), rice (Kyozuka et al., 1988), sugarcane (Chen, et al., 1988), and wheat (Chang et al., 1991) such cultures were an excellent source for protoplast regeneration. We have now found that in cassava FEC is the only tissue from which protoplasts can be isolated which are able to regenerate into plants sofar. We have further found that FEC can be used to regenerate cassava plants which tubers contain starch containing substantially no amylose.

SUMMARY OF THE INVENTION

Thus the present invention provides a method for producing protoplasts of cassava or a closely related species, which protoplasts are capable of regeneration into plants, comprising producing friable embryogenic callus from explants of cassava or a closely related species and isolating protoplasts from said friable embryogenic callus. It appears, as will be described below, that for obtaining suitable protoplasts the culture in solution of the FEC is quite important. Therefore the present invention further provides a method wherein the friable embryogenic callus is subjected to culture in a liquid medium.

Protoplasts are preferably produced by subjecting plant cells to enzymatic breakdown of the cell walls. The invention thus provides a method wherein a mixture of cell wall degrading enzymes, such as a cellulase, a pectolyase and/or a macerozyme are used to produce protoplasts.

It also appears that the method according to the invention works best when the plants from which explants are to be taken are pretreated. Therefore the invention provides a method wherein the plants from which explants are taken are pretreated with an auxin as described below.

On the explants preferably embryogenesis is induced resulting in an invented method wherein the friable embryogenic callus is produced from primary, secondary or cyclic embryogenic tissue. The reason is explained in the detailed description. Protoplasts obtainable by a method as disclosed above are also part of the invention.

An important reason for wanting to have protoplasts which can be regenerated into plants is of course that protoplasts can be easily transformed or transduced or provided with additional genetic information by any other suitable method. Thus one is now able to provide cassava plants or closely related species with genetic material of interest. The invention thus also provides a method for transforming (defined as providing with in any suitable manner) a protoplast of a cassava or a closely related species by providing said protoplast with additional genetic information through infection by a bacterium comprising said additional genetic information such as *Agrobacterium tumefaciens*, by electroporation or chemical poration providing a vector comprising said additional genetic information or by particle bombardment wherein the particles are coated with the additional genetic information, wherein a protoplast obtainable from friable embryogenic callus is transformed. The invention also encompasses transformed protoplasts obtainable by such a method.

Below a short introduction is given on the usefulness of transforming plants, such as cassava.

Application of plant gene technology encompasses a multitude of different techniques ranging from isolation of useful genes, their characterization and manipulation, to the reintroduction of modified constructs into the plants (Lonsdale, 1987). Plant gene technology will catalyze progress in plant breeding, as is exemplified by a few examples of transgenic crops like rice (Chen et al., 1987; Shimamoto et al., 1989), maize (Gordon-Kamm et al., 1990; Vain et al., 1993), wheat (Marks et al., 1989), and potato (De Block, 1988; Visser et al., 1989). Rapid progress in gene technology has allowed insight into the complex molecular mechanism of plant pathogen recognition and the natural defense strategies of host plants. This technology can also be used for controlled and efficient identification of desirable genotypes, far beyond the possibilities of classical breeding.

For instance electroporation of protoplasts derived from suspension cultures led to the transformation of maize (Rhodes et al., 1988), rice (Toriyama et al., 1988) and orchardgrass (Horn et al., 1988).

Successful attempts have been made to improve resistance against pathogenic viruses like tobamovirus in tobacco (Powel Abel et al., 1986), potexvirus in potato (Hoekema et al., 1989) and in papaya (Fitch et al., 1992). In the above examples the introduced trait was based on expressing of single genes that are coding for the coat protein. In cassava, African cassava mosaic virus (ACMV) and cassava common mosaic virus (CCMV) may be controlled by the coat protein-mediated resistance technique (Fauquet et al., 1992). The genes encoding key enzymes of cyanogenesis have been cloned (Hughes et al., 1994) which makes manipulation of cassava cyanogenesis by genetic transformation using the antisense approach feasible. Another embodiment of the invention is the manipulation of starch in the cassava tubers.

Thus the present invention provides a transformed protoplast wherein the additional genetic information comprises an antisense construct, particularly one wherein the antisense construct is capable of inhibiting the amylose synthesis pathway.

A protoplast cannot grow in the field, nor can it be harvested. Though protoplasts are necessary for transformation, it must be possible to regenerate said protoplasts into embryos and/or plants. This is a very important embodiment of the invention, because cassava has been shown to be difficult to regenerate from protoplasts. The detailed description explains how this may be achieved. For further information reference is made to the thesis written by E. Sofiari titled Regeneration and Transformation of Cassava (*Manihot Esculenta* Crantz.), a copy of which is enclosed with the present application, which is incorporated herein by reference. Thus the invention provides a method for regenerating plants from protoplasts wherein a protoplast according to the invention is induced to produce an embryo, which embryo is consequently induced to produce a plant.

The plants obtainable by said method are also part of the invention, in particular plants wherein the tubers contain essentially no amylose.

In addition, the invention provides a method for obtaining starch from the tubers of said cassava plants. The method can be carried out in a manner essentially similar to a method for isolating starch from potato tubers. In one embodiment of the invention, the method comprises the steps of washing the tubers, followed by grating and milling them. Subsequently, the starch is separated from fibers and juice in separators, e.g. centrifuges or hydrocyclones. The isolated starch may then be sieved, washed and dried. Washing may be carried out in hydrocyclones. Drying may be carried out in vacuum filters and drying towers.

The starch obtained from cassava tubers having an increased amylopectin content is also part of the invention. This starch preferably contains essentially no amylose, by it is meant that it preferably has an amylopectin content of at least about 90 wt. %, more preferably at least about 95 wt. %, most preferably at least about 98 wt. %, based on the (dry substance) weight of the starch. As used herein, amylopectin starch or low amylose starch is intended to mean starch obtained from a plant having such an increased amylopectin content. In addition, the starch has a number of distinct properties, such as molecular weight, intrinsic viscosity, particle size, and chain length distribution, which will be further elucidated below.

DETAILED DESCRIPTION OF THE INVENTION

Initiation of FEC

The procedure to obtain FEC is outlined in FIG. 1. It starts with the induction of primary embryos. Primary embryos are formed in a two step procedure. In the first step explants are cultured on medium supplemented with salts and vitamins (preferably Murashige and Skoog (1962)), a carbohydrate source (for example 20 g/l sucrose) and an auxin (e.g. 1–8 mg/l picloram, or dicamba or 2,4-D) for the initiation of embryos. After 10 to 15 days on this first medium bipolar torpedo shaped embryos are formed. Torpedo shaped embryos possess a clear hypocotyl and cotyledon primordia. After transfer of the explants with torpedo shaped embryos to a step 2 medium (the same medium as step 1 but without an auxin, with eventually the addition of cytokinins) the torpedo shaped embryos become mature. Mature embryos possess large green cotyledons.

Zygotic embryos (Stamp and Henshaw 1982; Konan et al., 1994), young leaf explants or apical meristems (Stamp and Henshaw, 1987a; Szabados et al., 1987; Mroginsky and Scocchi, 1993; Raemakers 1993a; Narayanaswamy et al., 1995) and floral tissue (Mukherjee, 1995, Woodward and Puonti-Kaerlas, 2001) can be used to obtain primary embryos. In this way many different genotypes were evaluated for their ability to form primary embryos. In this protocol primary somatic embryos were only formed after culture on solid medium and never after culture in liquid medium. Furthermore, somatic embryos (primary) were only observed if the auxins Picloram, Dicamba or 2,4-D were used and not with IAA, IBA or NAA.

In the presently used protocol there is genotypic variation in the number of mature embryos formed per cultured explant. The genotypes M.Col1505, M.Col22 and Gading gave the highest numbers of mature embryos per cultured leaf explant (ME/CLE). However, the number of mature embryos formed was low. In M.Col22 a maximum of 22% of the leaf explants isolated from in vitro grown plants and cultured on a step 1 medium with 4 mg/l 2,4-D, formed ME with a maximum number of 0.8 ME/CLE. On a step 1 medium with 8 mg/l 2,4-D a maximum of 49% of the leaf explants formed ME with a maximum number of 3.5 ME/CLE. Higher 2,4-D concentrations did not further improve the embryogenic capacity of explants.

In an attempt to improve the capacity of leaf explants to produce primary somatic embryos, donor plants were grown under different conditions. Growth of in vitro donor plants under different light regimes (8, 12, 16 or 24 hours) had no influence on the embryogenic response. However, a reduction of the light intensity had a positive effect. The best results were obtained with leaf explants isolated of donor plants grown at 8 $\mu Em^{-2}s^{-1}$ and cultured on a step 1 medium.

Other investigators have shown that in certain genotypes, Dicamba (1–66 mg/l) and Picloram (1–12 mg/l) are superior to 2,4D for inducing primary embryogenesis (Ng 1992; Sudarmonowati and Henshaw, 1993; Taylor and Henshaw, 1993). Mathews et al. (1993) improved the efficiency of primary embryogenesis in the genotype M.Col1505 by transferring explants after 15 days of step 1 medium to a growth regulator-free medium supplemented with 0.5% charcoal. On this medium maturation was improved and as a result the number of mature embryos increased from 0.4 in the control to 3,4 ME/CLE. The best results were obtained if donor plants were pretreated with auxins as 2,4-D or picloram or Dicamba. For this, plants were grown in liquid MS20 medium and supplied with the auxin (final concentration 8 mg/l) after 12 days of growth. Two days later leaf explants were isolated of the donor plants and cultured on step 1 medium with 8 mg/l 2,4-D, picloram or Dicamba. In the clone M.Col22 this resulted in a production of 9.4 ME/CLE. This was significantly higher than in the $H_2O$-treated control-plants, where 3.5 ME/CLE were produced (Table 3).

The general applicability of the auxin pretreatment was tested on several different genotypes. Without a pretreatment of donor plants two genotypes formed ME and at low frequency. After a pretreatment of donor plants, leaf explants of almost all genotypes formed ME.

Eventually we were able to obtain mature primary somatic embryos from 24 of the 28 tested genotypes (Table 1, except TMS30221, TMS30001, TMS30572 and Sao Paolo). These data suggest that almost all genotypes in cassava can undergo somatic embryogenis and up till now it has been shown that in more than 60 genotypes it has been shown that they can undergo primary somatic embryogenesis (Thro et al., 1999).

Primary somatic embryos derived from zygotic embryos and from leaves have been used as explants to initiate secondary embryos (Stamp and Henshaw, 1987b; Szabados et al., 1987; Mathews et al., 1993; Raemakers et al., 1993bc; Luong et al., 1995). Continuous culture of somatic embryos on auxin supplemented medium resulted in a cyclic system of somatic embryogenesis. The way of subculturing somatic embryos for secondary embryogenesis seemed to influence the morphology of the embryogenic tissue. Clumps of somatic embryos recultured monthly on solid 2,4D containing medium in the dark developed into finger-like embryo initials formed on the top of older embryos. The embryos did not pass the torpedo-shaped stage.

Further development occurred if the clumps with embryos were transferred to step 2 medium in the light (Szabados 1987). Normally mature somatic embryos were cultured in step 1 medium in the light and twenty days later the explants were transferred to step 2 medium for maturation. In this system embryos developed to maturity and mature embryos with large green cotyledons were used to start a new cycle of embryogenesis whereas in the system of others torpedo shaped embryos were used to start a new cycle of secondary somatic embryogenesis.

This system of multiplication of mature embryos has been tested in 14 20 of the in Table 1 mentioned genotypes. Despite the fact that in most genotypes only a few mature primary embryos were available, all genotypes, except one, gave new mature embryos after culture on 2,4-D supplemented medium, in a much higher frequency as observed for primary somatic embryogenesis (Raemakers et al. 1993b,c, 2000, 2001, Sofiari et al., 1996). Embryogenicity was maintained by regular subculture of mature embryos for more than one year (Szabados et al., 1987; Mathews et al., 1993; Raemakers, 1993). New somatic embryos were formed both in liquid and solid medium. In all the genotypes it was observed that in liquid medium more embryos were formed than in solid medium and that fragmentation of embryos before the start of a new cycle of secondary somatic embryogenesis increased the production compared to whole embryos. In for example M.Col22 whole embryos cultured on solid medium produced 8 embryos per cultured embryo, whereas fragmented embryos cultured in liquid medium produced 32 embryos per cultured embryo (Raemakers et al., 1993c). Not only, 2,4-D, Picloram and Dicamba, but also NAA had the capacity to induce secondary embryogenesis. IBA and IAA did not induce secondary embryogenesis. NAA has been used successfully in Adira 1, Adira 4, Gading, line 11, M.Col22, M.Col1505, TMS90853 and Gading (Sofiari, 1996). In general more mature embryos were produced in NAA supplemented medium than in 2,4-D, Picloram or Dicamba supplemented medium. Furthermore, the development of NAA induced embryos was faster than with 2,4-D, Dicamba or Picloram. Shortening the culture duration has a beneficial effect, particularly, when operating on a large scale.

Histologically, the by 2,4-D newly induced secondary embryos were attached vertically to the explants whereas those by NAA were horizontally.

Some scientists have still a problem in obtaining embryogenic cultures in certain genotypes of cassava (Mroginski and Scocchi, 1992; Taylor et al., 1992; Narayanaswamy et al., 1995; Sudarmonowati and Bachtiar, 1995). The main problem is not that embryogenic tissue from primary explants can be obtained, but the large scale multiplication of this tissue by secondary embryogenesis. For this purpose, either tissue consisting of torpedo shaped embryos or mature embryos can be used. Multiplication of torpedo shaped embryos is highly genotype dependent, while multiplication of mature embryos is largely genotype independent (Raemakers, 1993). Both primary and secondary somatic embryogenesis are characterized by the formation of propagules with a bipolar structure. These bipolar torpedo shaped embryos are already formed on the auxin supplemented step 1 medium. Therefore, Taylor et al., (1995) proposed the term organized embryogenesis. Organized cells are defined as a group of actively dividing cells, having the tissues and organs formed into a characteristic unified whole (Walker, 1989).

A less organized type of somatic embryogenesis was developed by Taylor et al. (1995). With continuous selection, organized embryogenic tissue cultured on a Gresshoff and Doy (1972) medium salts and vitamins supplemented with 10 mg/l Picloram (GD2) converted gradually into a less organized tissue. This tissue consisted of a callus-like mass of (pro-)globular embryos which was very friable. Therefore, this tissue was called friable embryogenic callus (FEC). The cells in FEC are continuously in a state where they break away from group control and because of that they are not organized into a unified structure. FEC is maintained on a medium consisting of Gresshoff and Doy (1972) vitamins and salts, 7 g/l Daichin agar, 20 g/l sucrose and 10 mg/l Picloram (solid GD2). Every three weeks the friable embryos were subcultured on the above mentioned medium. In order to initiate liquid suspension cultures 0.5 g of friable embryos was transferred in a flask of 200 ml with 50 ml of liquid medium supplemented with Schenk and Hildebrandt (1972) salts and vitamins, 60 g/l sucrose and 10 mg/l Picloram (liquid SH6). The medium was refreshed every 2–7 days and after 14 days the content of each flask was divided over 5 new flasks. The pH was adjusted to 5.7 before autoclaving. The temperature in the growth chamber was 30° C., the photoperiod 12 hours and the irradiance 40 $\mu molm^{-2}s^{-1}$. Suspension cultures were initiated by culturing FEC in Schenk and Hildebrandt (1972) medium supplemented with 6% (w/v) sucrose and 10 mg/i Picloram (SH6). Every 2–3 days this medium was refreshed.

To keep a culture in a highly friable state the FEC has to be sieved once in two months. In practice the part of the FEC which will go through a sieve with a mesh of 1 $mm^2$ will be used for subculture.

FEC will almost never form torpedo shaped embryos on the GD2 or in SH6 medium. Torpedo shaped and subsequent mature embryos are formed if FEC is cultured on maturation medium. Maturation medium consist of Murashige and Skoog (1962) salts and vitamins, and 1 mg/l picloram. This maturation medium was refreshed every 3 weeks.

Mature embryos could be induced into secondary somatic embryogenesis by culturing on MS20 medium supplemented with 2,4-D, picloram, Dicamba or NAA. Primary and secondary somatic embryogenesis are relatively easy to establish in a wide range of genotypes (see Table 1), while FEC is for the time being restricted to a few genotypes. The prospect of FEC for a new system of somatic embryogenesis and genetic transformation is promising, although further research is needed to make this system applicable to more genotypes. Essential for this process is the availability of high quality organized tissue and the ability of this tissue to convert into FEC. Taylor et al. (1995) "used organized embryogenic tissues" which were multiplied at the torpedo shaped state to initiate FEC. In this case two steps (initiation of organized. tissue and conversion into unorganized tissue) are determinative for the successful initiation of FEC. Both steps are genotype dependent. If organized tissue is multiplied in the mature state as described by Raemakers (1993) then only the ability of this tissue to convert into FEC is a determinative step to initiate FEC. It remains to be investigated whether or not organized tissue can be used as starting material. If organized tissue cannot be used, then this tissue should be first multiplied in the immature state before it can be used to initiate FEC. This is readily accomplished by, either culturing explants at a high density or by reducing the cyclic duration.

FEC lines have been obtained in R60, R90, M7, TMS60444 and Adira 4 (Raemakers et al., 2000, 2001). Plant regeneration from FEC has been achieved in R60, R90, M7, TMS60444 and Adira 4 (Raemakers et al., 2000, 2001). Taylor et all. (2000) has obtained FEC lines in the genotypes line 2, M.col1505, TMS90853, Kataoli and Bonoua Rouge.

Regeneration of Plants from Protoplasts

Isolation of Protoplasts

For protoplast isolation both FEC cultured on solid GD2 or liquid SH6 can be used. However, the highest yield of protoplasts was obtained from FEC which has been cultured for 1 to 3 weeks in liquid SH6.

Two gram of FEC was placed in Petri dishes (Ø 9 cm) containing 10 ml of cell wall digestion solution. Cell wall digestion solution consisted of a mixture of cell wall degrading enzymes; 10 mg/l pectolyase, 10 g/l cellulose, 200 mg/l macero enzyme growth regulators (NAA 1 mg/l, 2,4-D 1 mg/l, Zeatin 1 mg/l); major salts (368 mg/l $CaCl_2$; 34 mg/l $KH_2PO_4$; 740 mg/$KNO_3$; 492 mg/l $MgSO_4.7H_2O$); minor salts (19.2 mg/l NA-EDTA; 14 mg/l $FeSO_4.7H_2O$) and osmoticum (91 g/l D-mannitol) and 0.5 g/l MES. The cell wall degrading enzymes cellulase (1–10 g/l) plus Macerozyme (200 mg/l) were successful for protoplast isolation. The extra addition of Pectolyase (0.001–0.01 g/l) and/or Driselase (0.02 g/l) increased the yield of protoplasts. After 18 h of incubation, 10 ml of washing medium was added to the solution. Washing medium with an osmolarity 0.530 mOsm/kg consisted of major salts (see cell wall digestion solution), 45.5 g/l mannitol and 7.3 g/l NaCl. The digested tissue was filtered through a 73 μM pore size filter (PA 55/34 Nybolt-Switzerland) into a 250 ml beaker glass. The filtrate was divided equally over two 12 ml conical screw cap tubes, and centrifuged at 600 rpm for 3 min. (Mistral 2000). The washing procedure was repeated once after removal of the supernatant. The protoplast solution was resuspended by floating on 9.5 ml solution containing major and minor salts (see cell wall digestion solution) and 105 μl sucrose. The pH was 5.8 and the osmolarity 0.650 mOsm. The solution with protoplasts was allowed to equilibrate for 5 minutes before 0.5 ml of washing medium was gently added on the top. After centrifugation at 700 rpm for 15 min. (Mistral 2000), the protoplasts were concentrated in a band between the sucrose and washing medium. The protoplast layer was harvested with a pasteur pipette and the yield was counted in a standard haemocytometer chamber.

Protoplast culture

Protoplasts were cultured in media solidified with agarose 0.2% w/v (Dons en Bouwer, 1986) in petri dishes containing 10 ml of the same liquid medium. The following media resulted in the formation of micro callus:

TM2G medium (Wolters et al., 1991) supplemented with only auxins (0.1–10 mg/l NAA or 0.1–10 mg/l Picloram, or 0.1–10 mg/l IAA, or 0.1–10 mg/l 2,4-D, or 0.1–10 mg/l Dicamba, or 0.1–10 mg/l, or 0.1–10 mg/l) or auxins plus cytokinins (0.01–1 mg/l zeatin, 0.01–1 mg/l 2-iP, 0.01–1 mg/l BA, 0.01–1 mg/l TDZ, 0.01–1 mg/l kinetin).

medium A (Murashige and Skoog (1962) salts and vitamins, 4.5 g/l myo-inositol, 4.55 g/l mannitol, 3.8 g/l xylitol, 4.55 g/l sorbitol, 0.098 g/l MES, 40 mg/l adeninsulphate and 150 mg/l casein hydrolysate, 0.5 mg/l d-calcium-panthotenate, 0.1 mg/l choline-chloride, 0.5 mg/l ascorbic acid, 2.5 mg/l nicotinic acid, 1 mg/l pyridoxine-HCl, 10 mg/l thiamine-HCl, 0.5 mg/l folic acid, 0.05 mg/l biotine, 0.5 mg/l glycine, 0.1 mg/l L-cysteine and 0.25 mg/l riboflavin and 59.40 g/l glucose) supplemented with only auxins (0.1–10 mg/l NAA or 0.1–10 mg/l Picloram, or 0.1–10 mg/l IAA, or 0.1–10 mg/l 2,4-D, or 0.1–10 mg/l Dicamba plus cytokinins (0.01–1 mg/l zeatin, 0.01–1 mg/l 2-iP, 0.01–1 mg/l BA, 0.01–1 mg/l TDZ, 0.01–1 mg/l kinetin).

The media were refreshed every 10 days, by replacing 9 ml with fresh medium. After two months of culture in the first medium, high quality FEC was selected and either culture for further proliferation or for maturation. For proliferation FEC was transferred to Gresshoff and Doy (1974) medium supplemented with 40 g/l sucrose, 7 g/l Daichin agar and 2 mg/l picloram (GD4). After 3 weeks the FEC was transferred to a Gresshoff and Doy medium supplemented with 20 g/l sucrose, 7 g/l agar and 10 mg/l Picloram (GD2). Suspension cultures were initiated by transferring 1.0 g of FEC to liquid SH6% medium supplemented with 10 mg/l Picloram. Two weeks later the suspension was divided over new flasks with an initial packed cell volume of 1.0 ml.

After 2 months of culture, $10^4$ protoplasts cultured in TM2G supplemented with 0.5 mg/l NAA and 1 mg/l Zeatin at a density of $10^5$/ml produced 1058 micro-calli, whereas $10^4$ protoplasts cultured at a density of $10^6$/ml only produced 64 micro-calli.

Replacing TM2G medium with medium A reduced at both densities the number of micro-calli significantly. At this stage at least three types of calli could be distinguished. One type consisted of globular shaped embryos which were mostly observed in protoplasts cultured at a density of $10^6$. Some of them developed cotyledon like structures, light green in color. However, these embryos could not be germinated properly. Another type was fast growing and consisted of a large compact callus, they were observed in protoplast cultures of both densities. This callus never developed embryos. The third type was highly friable callus and was observed at both densities. At a density of $2–5 \times 10^5$ (medium TM2G) about 60% of the calli were friable and embryogenic. The FEC was either subcultured for further proliferation or for maturation.

Proliferation of FEC Derived from Protoplasts

Following selection of FEC, 0.1 g of it cultured for three weeks on GD 4 plus 2 mg/l Picloram increased into 0.7 g of tissue. More than 95% of the tissue consisted of high quality FEC. Subsequently, this tissue was maintained by subcultures of three weeks on GD2 medium supplemented with 10 mg/l Picloram. To initiate suspension cultures FEC was transferred to liquid medium. The increase in packed cell volume (PCV) of this material was slightly higher than that of the original material (data not shown).

Maturation of FEC Derived from Protoplasts

In an attempt to induce maturation of embryos, FEC isolated after two months of culture in TM2G was cultured on maturation medium. Maturation medium consisted of Murashige and Skoog (1962) salts and vitamins, 10 g/l Daichin agar, 0.1 µl myo-inositol, 20 g/l sucrose, 18.2 g/l mannitol, 0.48 g/l MES, 0.1 g/l casein hydrolysate, 0.08 g/l adenine sulphate, 0.5 mg/l d-calcium-panthotenate, 0.1 mg/l choline chloride, 0.5 mg/l ascorbic acid, 2. Mg/l nicotinic acid, 1 mg/l pyridoxine-HCl, 10 mg/l thiamine HCl, 0.5 mg/l folic acid, 0.05 mg/l biotin, 0.5 mg/l glycine, 0.1 mg/l L-cysteine, 0.25 mg/l riboflavin and 1 mg/l picloram. This maturation medium was refreshed every 3 weeks.

On this medium there is a gradual shift from proliferation to maturation. As a result the packed cell volume had increased with a factor 4 after two weeks of culture in liquid maturation medium. Also after transfer to solid maturation medium there is proliferation. After two weeks on solid medium most of the embryos had reached a globular shape and only a few of these globular embryos developed further. The first torpedo shaped embryos became visible after one month of culture on solid maturation medium. The number of mature and torpedo shaped embryos was not correlated with the plating efficiency but with the density of the initially cultured protoplasts. No such embryos were obtained if protoplasts were cultured on TM2G without growth regulators. The highest number of mature and torpedo shaped embryos was formed from protoplasts cultured on TM2G supplemented with 0.5 mg/l NAA and 1 mg/l Zeatin. If NAA was replaced by Picloram then the number of torpedo shaped and mature embryos was significantly lower (Table 2). From the tested Picloram concentrations 2 mg/l gave the best results. After 3 months of culture between 60 and 200 torpedo shaped and mature embryos were isolated per agarose drop. Torpedo shaped embryos became mature at high frequency if they were cultured on fresh maturation medium or on MS2 plus 0.1 mg/l BAP.

Secondary Somatic Embryogenesis and Germination of Mature Embryos Derived from Protoplasts Only a few torpedo shaped embryos formed secondary embryos if cultured on liquid or solid MS2 medium supplemented with 10 mg/l NAA or 8 mg/l 2,4-D (data not shown). Mature embryos were better explants for secondary embryogenesis. In both liquid and solid medium 2,4-D was superior for induction of secondary embryogenesis as compared to NAA. If mature embryos were first cultured in 2,4-D and than in liquid NAA the response was comparable with culture in 2,4-D alone. Also embryos which first had undergone a cycle of secondary somatic embryogenesis in medium with 2,4-D, produced highly efficient secondary embryos in MS20 supplemented with 10 mg/l NAA.

The germination of cyclic or secondary somatic embryos, induced in liquid medium by the auxins 2,4-dichlorophenoxyacetic acid (2,4-D) or naphthalene acetic acid (NAA), was compared. In all genotypes desiccation stimulated normal germination of NAA induced embryos. However, the desiccated embryos, required a medium supplemented with cytokinins such as benzytaminopurine (BAP) for high frequency germination. The morphology of the resulting seedling was dependent on the concentration of BAP. With 1 mg/l BAP plants with thick and short taproots and branched shoots with short internodes were formed. With 0.1 mg/l BAP the taproots were thin and slender and the shoot had only one or two apical meristems. If the embryos were desiccated sub-optimally, higher concentrations of BAP were needed than if the embryos were optimally desiccated to stimulate germination. Also desiccated embryos which were cultured in the dark required a lower concentration of BAP and, furthermore, these embryos germinated faster than embryos cultured in the light. Complete plants were obtained four weeks after the start of somatic embryo induction. 2,4-D induced embryos showed a different response. In only one genotype desiccation enhanced germination of 2,4-D induced embryos and in three other genotypes it did not. In all genotypes desiccation stimulated root formation. Embryos cultured in the dark formed predominantly adventitious roots, whereas embryos cultured in the light formed predominantly taproots.

Gene Transfer Systems

Over the past years several transfer techniques of DNA to plant protoplasts have been developed such as silicon fibers (Kaeppler et al., 1990), microinjection (De Laat and Blaas, 1987) and electrophoresis (Griesbach and Hammond, 1993). The most commonly used and potentially-applicable ones are *Agrobacterium*-mediated gene delivery, microprojectile/particle bombardment and protoplast electroporation.

The *Agrobacterium tumefaciens* DNA delivery system is the most commonly used technique. It probably relates to the first invention of DNA delivery in plants by this method. Initially it was limited to Kalanchoe and Solanaceae, particularly tobacco. Nowadays, the use of *Agrobacterium*-mediated transformation has changed dramatically, it is possible to transform a wide range of plants including the most important monocots like maize and rice with a limitation in monocots (reviewed by Wordragen and Dons, 1992).

Although cassava is a host for *Agrobacterium* it has proven to be not highly amenable to it.

FEC from cassava has also been transformed efficiently via *Agrobacterium tumefaciens* (Raemakers et al., 2000, Schreuder et al., 2001). The method described by Raemakers et al., 2000 and Schreuder et al., 2001 has been used successfully to produce genetic modified plants from the genotypes Adira 4 and TMS604444 carrying the antisense gbss gene under control of the CaMV promoter.

In principle protoplasts are the most ideal explants for DNA delivery. They can be cultured as single cells that produce multicellular colonies from which plants develop. Plants derived from protoplasts are generally clonal in origin. This provides a useful tool for any transformation system, because it will eliminate chimerism in transgenic plants. The use of protoplasts is, however, hampered by the regeneration system which is highly species dependent. For transformation, protoplasts can be used in conjunction with PEG to alter the plasma membrane which causes reversible permeabilization that enables the DNA to enter the cytoplasm as was demonstrated, for example, in *Lolium multiform* (Potrykus et al., 1985) and *Triticum monococcum* (Lörz et al., 1985). Another technique to increase the permeability of plasma membranes and even cell walls to DNA is by electroporation (for review see Jones et al., 1987). In this method electrical pulses enable the DNA to enter the cells. Rice was the first crop in which fertile transgenic plants resulted from protoplast electroporation (Shimamoto et al., 1989).

The use of particle bombardment or biolistics to deliver foreign DNA provides an alternative method in cassava transformation. Particle bombardment is the only procedure capable of delivering DNA into cells almost in any tissue. The first transgenic plant obtained by using this method was in tobacco (Klein et al., 1989). Following this successful transformation method, particle bombardment is widely used in plants which are less amenable to *Agrobacterium* infection, particularly monocots. Improvement of several DNA delivery devices to accelerate the particle (microprojectile) has resulted in the most recent model the Biolistic™ PDS-1000 (Blo-Rad Laboratories, Richmond, Calif.). Those devices are available commercially, however the price is relatively high at present. Tungsten or gold particles, coated with DNA, are commonly used as microprojectiles to deliver DNA into the target tissue (reviewed by Songstad et al., 1995).

Selection and Reporter Genes used in Genetic Modifications

To be able to identify transformed cells, the gene of interest is coupled to a selectable marker gene. This marker gene is necessary to select transformed cells. Selection can be based on a visual characteristic of the transformed cell/tissue. An example is the luciferase gene isolated from the firefly. Plant cells expressing this gene and supplied with substrate (luciferin) will emit light which can be detected with special equipment (Ow et al., 1986). Another way to select transformed tissue is the introduction of a gene which encodes resistance to antibiotics or herbicides (Thompson et al., 1987; Gordon-Kamm et al., 1990).

A number of antibiotics and herbicides has been used as selective agent in plant transformation. In cereals resistance to the herbicide phosphinothricin (PPT) was chosen for the selection of transgenic plants (Cao et al., 1990). In *Carica papaya* (Fitch et al., 1994), *Vitis vinifera* (Nakano et al., 1994; Scorza et al., 1995), maize (Rhodes et al., 1988) and rice (Chen et al., 1987) the neomycine phosphothansferase (NPTII) gene, which confers resistance to kanamycin and related antibiotics (Fraley et al., 1986), was used as a selectable marker.

In cassava all above-mentioned systems of selection can be used, however PPT based selection has as advantage that it improves the ability of FEC to form mature embryos and in this way increase plant regeneration.

The following part describes how cassava plants genetically were modified with the aim to produce cassava plants with a high amylopectin content in their tuberous roots.

Isolation of the Cassava gbss Gene and Construction of a Plant Transformation Vector In a previous study the gbss gene was isolated from cassava using the potato gbss gene (Visser et al., 1989) as probe (Salehuzzaman et al., 1993). The gbss gene was subcloned in anti-sense orientation between the potato gbss promoter (Visser et al., 1991) and the nopaline synthase terminator in pUC19 resulting in the vector pAG61 (Salehuzzaman et al., 1993). Also other preferably tuberous root specific promoters such as protein synthesis elongation factor 1-alpha from cassava (Suhandono et al., 2001), cassava gbss or more general promoters such as CaMV can be used to direct expression of genes such as gbss.

The complete luciferase gene (BglII fragment) was isolated from pJIT100 (Guerineau et al., 1993) and inserted in the BamHI site of pAG61. This resulted in two different vectors: pGBSSas2 and pGBSSas7 (difference between the two vectors was the orientation of the luciferase and antisense gbss genes to each other). Both constructs were used successfully to produce cassava plants with a high amylopectin content.

Plant Material and Tissue Culture Media used

Plants of the genotype TMS60444 were maintained by monthly subculture of one node cuttings on medium supplemented with Murashige and Skoog (1962) salts and vitamins and 40 g/l sucrose (MS4). Friable embryogenic callus (FEC) lines were initiated as follows:

- isolation of meristems or immature leaves from donor plants
- cultured of meristems/leaves on MS40 supplemented with 6 mg/l NAA and 6 mg/l Picloram
- isolation of compact embryogenic tissue and cultured on a medium supplemented with Gresshoff and Doy (1974) salts and vitamins, 60 g/l sucrose and 10 mg/l Picloram (GD6).
- isolation of FEC (small clumps of aggregated, spherical units) which were cultured on GD6 medium. FEC was maintained by a 3 weeks subculture on GD6 medium. Liquid cultures were initiated by transferring 0.5 g of FEC into flask of 200 ml with 50 ml of liquid medium supplemented with Schenk and Hildebrandt (1972) salts and vitamins, 60 g/l sucrose and 10 mg/l Picloram (SH6). The medium was refreshed twice a week and after 2 weeks the content of a each flask was divided over 5 new flasks. The flasks were cultured on a rotary shaker (LAB-line Instruments Inc. Model 3519) at 120 rpm.

Coating of DNA on the Particles.

A method adjusted from Cabe et al. (1988) was used to coat DNA on the particles. Eighty μg of DNA (isolated using Wizard™ Maxipreps DNA purification system of Promega from the vectors pGBSSas2 and pGBSSas7) was mixed with 10 mg of gold particles (1.6 μm, BioRad), 30 μl 5 M NaCl, 5 μl 2 M tris HCl pH 8.0, 965 μL H2O, 100 μl 25% PEG 1550, 100 μL 0.1 M spermidine and 50 μl 2.5 M $CaCl_2$. After centrifugation the pellet was resuspended in 10 ml of absolute alcohol and briefly sonificated. Hundred sixty μL of the suspension was pipetted in the hole of a macrocarrier holder placed up side down on a macrocarrier. After 5 minutes the macro carrier holder was taken away. The macrocarrier covered with a thin layer of gold beads was dried in an oven (10 minutes, 40° C.) and used for bombardment.

Bombardment of FEC and Selection of Transgenic Plants

FEC cultured in liquid SH6 medium for at least 5 weeks, was sieved (mesh 1 mm) and collected. Hundred mg of FEC was spread on GD6 medium and bombarded using the BioRad PDS-1000He biolistic device (helium pressures 1100 p.s.i., 0.5 cm distance between rupture disc and the macrocarrier and between macrocarrier and the stopper plate, 5.0 cm distance between stopper plate and FEC, 27 inches Hg vacuum).

In total 212 and 184 Petri dishes with FEC from TMS60444 were bombarded with construct GBSSas2 or GBSSas7 respectively. After bombardment the bombarded FEC was cultured in plastic pots filled with liquid SH6 medium. Two weeks later the FEC was collected on solid GD6 medium and assayed for luciferase activity. Each luciferase (LUC) spot was subcultured as an individual line. In total 186 luc spots were produced with construct GBSSas2 and 222 with GBSS7. Because it was not possible to locate precisely which FEC unit contained LUC activity and to avoid loss of transgenic tissue, the tissue in a radius of 0.5–1 cm around the LUC spot was transferred in liquid SH6 medium. Two weeks later the FEC was assayed for luciferase activity. Lines without luciferase activity were discarded and lines with 4 or more spots were used for subclump division The lines with 1–3 spots were transferred again to liquid Sh6 medium and two weeks later the lines in which the number of spots had increased to 4 or more were used for sub clump division; the others were discarded.

Forty four lines were obtained from the bombardments with pGBSSas2 and 40 lines from the bombardments with pGBSSas7. The transgenic tissue was isolated and purified via a process called subclump division (Raemakers et al., 2000). Subclump division started with subculturing the tissues around (0.5 to 1 cm diameter) a luciferase positive spot. The tissue was divided as fine as possible on GD6 medium. Two weeks later the Petri dish was covered with small clumps of FEC tissue. Only the LUC positive clumps were subcultured. For this the clumps were divided in subclumps and cultured on GD6 medium. This selection procedure was repeated 1–2 times more before the tissue was cultured for plant regeneration. For this the 84 FEC lines were subcultured every 2–3 weeks for 10–12 weeks on maturation medium (MS4 supplemented with 1 mg/l Picloram). Torpedo shaped somatic embryos were isolated from the FEC and cultured on MS4 supplemented with 0.1 mg/l BAP, which allowed further maturation. Mature somatic embryos were first cultured for two weeks in liquid and hereafter in solid germination medium (MS4+1 mg/l BAP). Plants were rooted on MS4 medium. Plants were obtained from 31 of the 44 GBSSas7 cultured lines and 27 of the 40 GBSSas7 cultured lines. These plants were first grown on Murashige and Skoog medium supplemented with 8% sucrose to allow starch disposition in the stems of the cassava plants (Salehuzzaman et al., 1994). The amylose/amylopectin ratio was visualised by iodine staining of cross sections of the in vitro thickened stems with Lugol's solution (I2:KI). The stained stem sections were visualised microscopically. In total 9 lines (3 from GBSSas2 and 6 from GBSSas7) yielded plants with an altered staining pattern, meaning that said plants had a an altered starch composition in the stems. These plants were transferred to the greenhouse to allow formation of tuberous roots. Three months later the roots were peeled and the central cylinder of the storage root was grounded in a laboratory blender in water with a small amount of $Na_2S_2O_5$. The slurry was transferred for starch isolation to a Sanamat. The water-starch granules suspension was transferred to centrifuge tubes and centrifuged. The starch was dried at 20 degrees Celsius for 3 days.

The amylopectin/amylose content was determined using the protocol described by Hovenkamp-Hermelink et al. (1988).

In total 2 lines (one from GBSSas2 and one from GBSSas7) had yielded plants which in both tests had a high amylopectin content. One year later the same plants were transferred again to the greenhouse. Starch of in total 30 plants of the two lines were analysed via iodine staining and via spectrophotometry. All plants had starch with a high amylopectin content. At the same moment starch was isolated from more than 3000 plants. This starch was analysed in three different laboratories and again it was shown that the starch contained a high percentage amylopectin.

Materials & Methods

| Samples | |
| --- | --- |
| Tapioca starch | control sample |
| Amylopectin tapioca starch | AFC3KD from Wageningen |
| Potato starch | Oostermoer 1998 |
| Amylopectin potato starch | Oostermoer 1996 |
| Corn starch | Meritena A |
| Waxy corn starch | Meritena 300 |

Methods

Nitrogen Content ($N_{total}$)

ISO 5378 (1978), Starch and derived products—Determination of nitrogen by the Kjeldahl method—Spectrophotometric method.

Particle Size Distribution

The particle size is measured with a Coulter Multisizer II, calibrated with Coulter calibration standard P.D.V.B. Latex lot F.34, diameter measuring tube 140 µm, number of measured classes 256, measuring range 3,1–107,7 µm (potato starches) and 2,8–82,0 µm (other starches). The samples are suspended in isotonic salt solution (Diluid™ azid free, J. T. Baker) and homogenized in a ultrasonic bath (Branson 5510).

Differential Scanning Calorimetry

Differential scanning calorimetry experiments are performed using a Perkin-Elmer DSC-7. At least 10 mg of starch and 40 mg of demineralised water are put in a stainless steel DSC-pan to obtain 80% water content thereby taking the water content of the starch into account. The DSC-pan is hermetically sealed and stored one night at room temperature to equilibrate. Next day, the sample is heated from 5 to 130° C. with a rate of 10° C./min.

Dry Substance Content

ISO 1666 (1997), Starch and derived products—Determination of moisture content—Oven drying method.

Ash Content

ISO 5984 (1978), Animal feeding stuffs—Determination of crude ash content.

Intrinsic Viscosity (IV)

The intrinsic viscosity is determined in a known manner with a Ubbelohde viscosity meter with 1 M sodium hydroxide as solvent and expressed in g/dl. As described in H. W. Leach in Cereal Chemistry, vol. 40, page 595 (1963).

Phosphor Content (P)

ISO 3946 (1982), Starch and derived products—Determination of total phosphorous content—Spectrophotometric method.

Viscosity Behavior

Determined with a Rapid Visco Analyser (RVA) from Newport Scientific. The measurements are carried out in a 6% concentration in demineralized water at 400 rpm. Temperature cycle: 2 min at 45° C., heating to 90° at 14° per min, 5 min at 90° and cooling to 30° at 14° per min.

Chain Length Distribution

The amylopectin starch is debranched with isoamylase, the resulting linear alfa-1,4 malto-oligosaccharides are measured with High Performance Anion Exchange Chromatography with a Pulsed Amperometric Detection System.

Materials & Methods

| Samples | |
|---|---|
| Tapioca starch | control sample |
| Amylopectin tapioca starch | AFC3KD from Wageningen |
| Potato starch | Oostermoer 1998 |
| Amylopectin potato starch | Oostermoer 1996 |
| Corn starch | Meritena A |
| Waxy corn starch | Meritena 300 |

Methods

Nitrogen Content ($N_{total}$)

ISO 5378 (1978), Starch and derived products—Determination of nitrogen by the Kjeldahl method—Spectrophotometric method.

Particle Size Distribution

The particle size is measured with a Coulter Multisizer II, calibrated with Coulter calibration standard P.D.V.B. Latex lot F.34, diameter measuring tube 140 μm, number of measured classes 256, measuring range 3,1–107,7 μm (potato starches) and 2,8–82,0 μm (other starches). The samples are suspended in isotonic salt solution (Diluid™ azid free, J. T. Baker) and homogenized in a ultrasonic bath (Branson 5510).

Differential Scanning Calorimetry

Differential scanning calorimetry experiments are performed using a Perkin-Elmer DSC-7. At least 10 mg of starch and 40 mg of demineralised water are put in a stainless steel DSC-pan to obtain 80% water content thereby taking the water content of the starch into account. The DSC-pan is hermetically sealed and stored one night at room temperature to equilibrate. Next day, the sample is heated from 5 to 130° C. with a rate of 10° C./min.

Dry Substance Content

ISO 1666 (1997), Starch and derived products—Determination of moisture content—Oven drying method.

Ash Content

ISO 5984 (1978), Animal feeding stuffs—Determination of crude ash content.

Intrinsic Viscosity (IV)

The intrinsic viscosity is determined in a known manner with a Ubbelohde viscosity meter with 1 M sodium hydroxide as solvent and expressed in g/dl. As described in H. W. Leach in Cereal Chemistry, vol. 40, page 595 (1963).

Phosphor Content (P)

ISO 3946 (1982), Starch and derived products—Determination of total phosphorous content—Spectrophotometric method.

Viscosity Behavior

Determined with a Rapid Visco Analyser (RVA) from Newport Scientific. The measurements are carried out in a 6% concentration in demineralized water at 400 rpm. Temperature cycle: 2 min at 45° C., heating to 90° at 14° per min, 5 min at 90° and cooling to 30° at 14° per min.

Chain Length Distribution

The amylopectin starch is debranched with isoamylase, the resulting linear alfa-1,4 malto-oligosaccharides are measured with High Performance Anion Exchange Chromatography with a Pulsed Amperometric Detection System.

Results

The results are shown in the following tables.

TABLE 1

| | Chain length distribution (weight average) | | | | | |
|---|---|---|---|---|---|---|
| | Cassava | Amylopectin Cassava | Maize | Waxy Maize | Potato | Amylopectin Potato |
| DP 6 t/m 9 | 4.1 (5.9) | 4.6 (5.7) | 2.4 (3.9) | 3.3 (3.7) | 2.1 (3.7) | 2.6 (3.9) |
| DP 6 t/m 12 | 14.7 (21.7) | 16.4 (20.4) | 11.2 (18.2) | 15.3 (17.0) | 7.6 (13.5) | 9.5 (14.1) |
| DP 13 t/m 24 | 31.9 (46.6) | 36.9 (46.0) | 33.2 (54.0) | 46.2 (51.4) | 29.2 (51.7) | 33.3 (49.4) |
| DP 25 t/m 40 | 14 (20.4) | 17.5 (21.8) | 13 (21.1) | 19.2 (21.4) | 12.6 (22.3) | 14.9 (22.1) |
| DP > 40 | 7.8 (11.4) | 9.4 (11.7) | 4.3 (7.0) | 8.9 (9.9) | 7.4 (13.1) | 9.8 (14.5) |
| Recovery (%) | 68.5 (100) | 80.2 (100) | 61.5 (100) | 89.9 (100) | 56.5 (100) | 67.4 (100) |

TABLE 2

| | Various parameters | | | |
|---|---|---|---|---|
| Parameter | Waxy Maize | Amylopectin cassava (ACS) | Amylopectin potato (APS) | Character ACS |
| RVA | | | | |
| Tg | 62.3° C. | 61.7° C. | 63.3° C. | Low Tg for ampec starch |
| Tg - Ttop | 10.0° C. | 5.9° C. | 5.8° C. | Fast dissolving |
| Ttop visco | 75 RVU | 112 RVU | 171 RVU | |
| Tend visco | 48 RVU | 87 RVU | 77 RVU | |
| Brabender | | | | |
| Tg | 66° C. | 60.5° C. | 61.5° C. | Low Tg for ampec starch |
| Tg - Ttop | 6.5° C. | 6° C. | 7° C. | Fast dissolving |
| Ttop visco | 685 BU | 990 BU | 1560 BU | |
| T20'90 | 250 BU | 290 BU | 440 BU | |
| Tend visco | 400 BU | 495 BU | 670 BU | |

TABLE 2-continued

Various parameters

| Parameter | Waxy Maize | Amylopectin cassava (ACS) | Amylopectin potato (APS) | Character ACS |
|---|---|---|---|---|
| Amylose content | | <1% | <1% | Schoch, detection level |
| Visco stability | Stable | Stable | Stable | No differences |
| Protein | 0.41 mg/g | 0.16 mg/g | 0.10 mg/g | Clear solution |
| Phosphate | <0.05 mg/g | 0.06 mg/g | 0.81 mg/g | Clear solution, viscosity level |
| Chain length distribution | 21 | 27 | 28 | |

TABLE 3

Various parameters

| | dry substance mg/g as is | ash mg/g ds | $N_{total}$ mg/g ds | P mg/g ds | IV dl/g ds |
|---|---|---|---|---|---|
| Tapioca | 860 | 3.5 | 0.11 | 0.06 | 2.4 |
| Amylopectin tapioca | 863 | 2.3 | 0.16 | 0.06 | 1.7 |
| Potato | 844 | 4.7 | 0.13 | 0.85 | 2.4 |
| Amylopectin potato | 856 | 4.7 | 0.10 | 0.81 | 1.8 |
| Maize | 879 | 1.1 | 0.53 | 0.18 | 1.7 |
| waxy maize | 881 | <1.0 | 0.41 | <0.05 | 1.6 |

TABLE 4

Particle size distribution

| | weight average μm | $d_{10}$ μm | $d_{50}$ μm | $d_{90}$ μm |
|---|---|---|---|---|
| Tapioca | 13.0 | 7.8 | 12.6 | 16.9 |
| Amylopectin tapioca | 14.0 | 7.7 | 13.0 | 19.2 |
| Potato | 42.9 | 23.0 | 42.4 | 63.3 |
| Amylopectin potato | 45.0 | 23.2 | 44.7 | 67.0 |
| Maize | 14.0 | 9.8 | 14.1 | 18.4 |
| waxy maize | 14.3 | 9.3 | 14.0 | 18.3 |

TABLE 5

Results of gelatinisation behaviour measured by DSC.

| | $T_{onset}$ (° C.) | $T_{peak}$ (° C.) | $T_{end}$ (° C.) | $\Delta T$ (° C.) | $\Delta H$ (J/g) |
|---|---|---|---|---|---|
| Tapioca | 60.2 ± 0.4 | 65.0 ± 0.6 | 72.8 ± 0.7 | 12.6 ± 0.3 | 19.19 ± 1.2 |
| Amylopectin tapioca | 61.7 ± 0.3 | 67.6 ± 1.0 | 75.9 ± 0.6 | 14.2 ± 0.4 | 19.11 ± 2.2 |
| Potato | 62.6 ± 0.3 | 67.3 ± 0.6 | 75.1 ± 0.9 | 12.5 ± 0.6 | 22.12 ± 2.7 |
| Amylopectin potato | 63.3 ± 0.3 | 69.1 ± 0.4 | 75.2 ± 0.6 | 11.9 ± 0.5 | 24.04 ± 1.4 |
| Maize | 67.4 ± 0.2 | 73.2 ± 0.3 | 79.3 ± 0.9 | 12.1 ± 0.9 | 15.92 ± 0.6 |
| waxy maize | 62.3 ± 0.3 | 72.3 ± 0.3 | 80.4 ± 0.2 | 18.1 ± 0.4 | 18.76 ± 0.8 |

Different Properties of Amylopectin Cassava Starch Compared to Waxy Maize Starch:
  Low Tg
  Fast dissolving starch (difference between Tgelatinization and Ttop)
  About 20% higher viscosity
  Less protein, low impurity level Properties Amylopectin Cassava Starch Compared to Amylopectin Potato Starch
  Somewhat lower Tg (<1 C)
  Fast dissolving starch, however the viscosity of APS is higher (delta C=6C–BU=1400)
  About 30% lower viscosity level
  Small granules
  Crystallinity

TABLE 6

Genotypes of cassava used for somatic embryogenesis.

| Indonesia | Nigeria | TMS90853 | M. Co122, | Sao Paolo |
|---|---|---|---|---|
| Adira 1 | TMS50395 | TMS30555 | Zimbabwe | Thailand |
| Tjurug | TMS60444 | TMS30211 | Line 11 | R5 |
| Adira 4 | TMS90059 | TMS30395 | M7 | KU50 |
| Mangi 4 | TMS30572 | TMS30001 | Venezuela | R60 |
| Gading | TMS4(2)1244 | Columbia | M.Ven77 | R90 |
| Faroka | TMS60506 | M. Col 1505 | Brasil | R1 |

TABLE 7

Influence of light intensity during growth of donor plants in vitro on the number of leaf explants responding with the formation of mature embryos and the number of mature embryos per cultured leaf explant (#ME/CLE).

| light intensity ($\mu Em^{-2}s^{-1}$) | number of explants | responding explants[a] | production (#ME/CLE[b]) |
|---|---|---|---|
| 40 | 48 | 18 b | 1.7 b |
| 28 | 48 | 26 ab | 4.9 ab |
| 8 | 48 | 31 a | 6.6 a |

[a,b]means with the same letter are not significantly different by respectively Chi-square test (p < 0.1) and by LSD test (p < 0.1)

TABLE 8

Influence of 2,4-D pretreatment on production of primary mature embryos (# mature embryos per cultured leaf explant isolated from in vitro plants), followed by the multiplication of mature embryos by secondary somatic embryogenesis in 11 Nigerian cassava genotypes and in M.Col22.

| embryogenesis | primary[a] | | secondary[b] |
|---|---|---|---|
| 2,4-D pretreatment | no | yes | |
| M.Col22 | 3.5 | 9.4 | 13.5 |
| TMS 30555 | 0 | 0.7 | 6.2 |
| TMS 50395 | 0 | <0.1 | 5.3 |
| TMS 60506 | 0 | <0.1 | 0 |
| TMS 90059 | 0 | <0.1 | 7.2 |
| TMS 30211 | 0 | 0 | — |
| TMS 60444 | 0 | 1.1 | 9.9 |
| TMS 30395 | 0 | 0.1 | 6.7 |
| TMS 90853 | <0.1 | 0.2 | 8.2 |
| TMS 4(2)1244 | <0.1 | 0 | 5.4 |
| TMS 30001 | 0 | 0 | — |
| TMS 30572 | 0 | 0 | — |

[a]average of three experiments (total 48–74 leaf explants),
[b]average of two experiments (total 24–48 ME explants).

Figure 1:
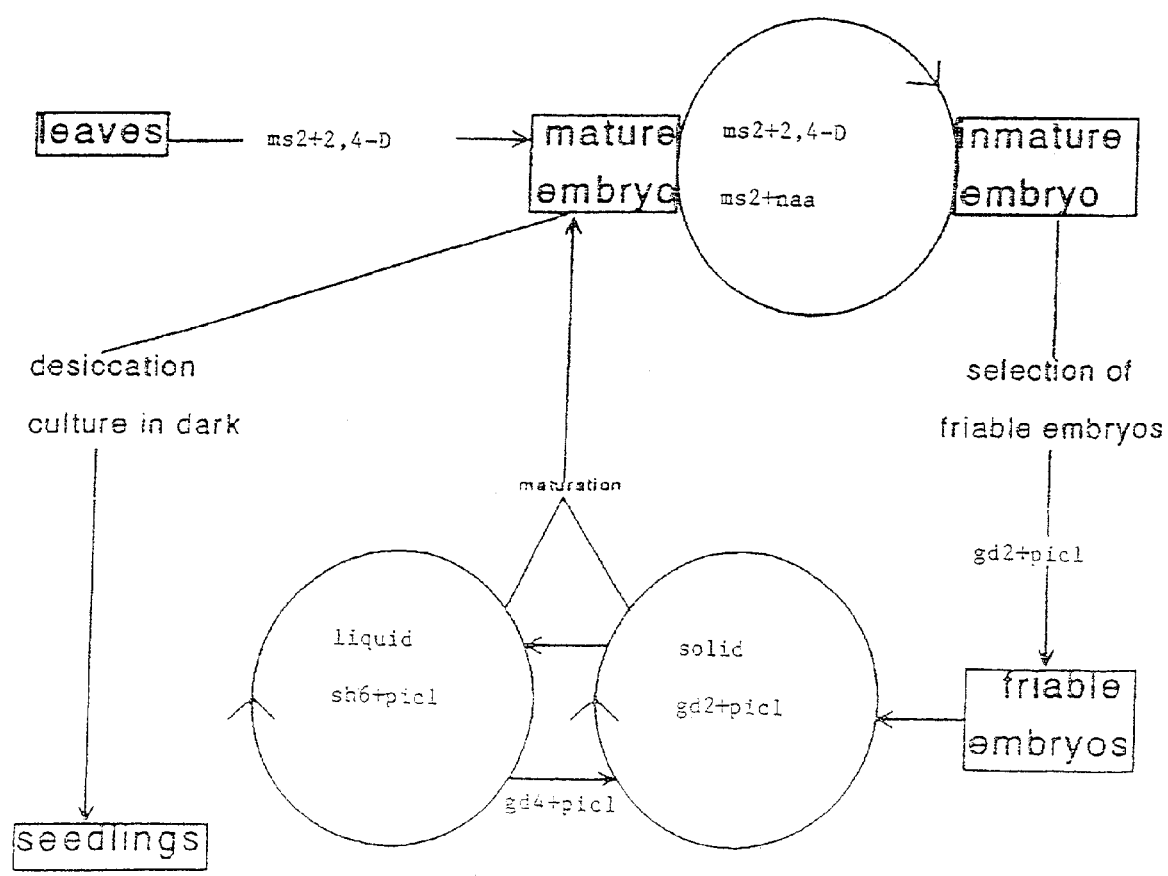
FIG. 1: Schematic representation of somatic embryogenesis in cassava, including primary, secondary somatic embryogenesis, selection of friable embryogenic callus, maturation and desiccation followed by germination.
gd2=medium supplemented with Gresshoff and Doy salts (1974) and vitamins plus 20 g/l sucrose.
gd4=medium supplemented with Gresshoff and Doy salts (1974) and vitamins plus 40 g/l sucrose.
ms2=medium supplemented with Murashige and Skoog salts and vitamins plus 20 g/l sucrose.
pic=10 mgl/l Picloram, NAA=10 mg/l naphthalene acetic acid, 2,4-D=8 mg/l, 2,4-dichiorophenoxy acetic acid.
sh6=medium supplemented with Schenk and Hildebrandt (1972) salts and vitamins plus 60 g/l sucrose.

Thus, the present invention also is intended to cover amylopectin cassava (tapioca) starch, both native and derivatized, and compositions containing such starch. The starch is useful in a wide variety of food, pharmaceutical, and industrial applications, either with or without chemical modification.

Amylopectin starch, as used herein, is intended to mean a starch or flour which has an amylopectin content substantially higher than that of regular cassava starch, particularly at least about 90%, more particularly at least about 95%, most particularly at least about 98% amylopectin by weight.

Amylopectin cassava starch may be obtained by the FEC method, supra. Also included in this invention are amylopectin cassava starches derived from amylopectin cassava plants which may be found in nature, obtained by standard breeding and crossbreeding techniques, or obtained by translocation, inversion, transformation or any other method of gene or chromosome engineering to include variations thereof, whereby the properties of the starch of this invention are obtained. In addition, starch extracted from a plant grown from artificial mutations and variations of the above generic composition which may be produced by known standard methods of mutation breeding is also applicable herein.

The substantially pure starch may be extracted from the root of a amylopectin cassava plant. Extraction may be by any method known in the art, including but not limited to pulverizing the root and separating the starch from the remaining components by water extraction.

The amylopectin cassava starches have lower levels of amylose and higher levels of amylopectin. The amylopectin cassava starches also have a higher viscosity than regular cassava starches, particularly at least about 30% greater than, more particularly at least 50% greater than, and most particularly at least about 80% greater than that of regular cassava starches. Particularly suitable amylopectin cassava starches are those which have a peak viscosity of at least about 1200, more particularly at least about 1300 as measure by Rapid Visco Analyzer using the method of Example 3a, infra.

The resultant native starch has properties and functionality which are unique and desirable in many applications.

Such native starches have the additional benefit of achieving the desired functionality without chemical modification. However, the present starches also may be modified to further enhance their properties and functionality. Any modifications known in the art may be used, including those which are chemical, physical, or enzymatic.

Chemical derivitization shall include those to form ethers, esters or half esters such as hydroxyalkyl ethers, acetates, phosphates, succinates, i.e., octenyl succinate, tertiary and quaternary amine ethers, etc., or by any other modification techniques known in the art.

Chemical modification of the present starch includes cross-linking. Any cross-linking agent known in the art may be employed for this purpose, including but not limited to epichlorohydrin, linear dicarboxylic acid anhydrides, citric acid acrolein, phosphorus oxychloride, adipic/acetic mixed acid anhydrides, trimetaphosphate salts, formaldehyde, cyanuric chloride, diioscyanates, and divinyl sulfones.

The present starches may be physically modified, such as by thermal inhibition described in WO 95/04082 (published Feb. 9, 1995) or by shear.

The present starches may also be enzymatically modified by one or more enzymes known in the art, including without limitation alpha-amylase, beta-amylase, glucoamylase, maltogenase, isoamylase and pullulanase.

The starches may also be pregelatinized. Exemplary processes for preparing pregelatinized starches are disclosed in U.S. Pat. No. 4,280,851 (Pitchon, et al.), U.S. Pat. No. 4,465,702 (Eastman, et al.), U.S. Pat. No. 5,037,929 (Rajagopalan), U.S. Pat. No. 5,131,953 (Kasica, et al.), and U.S. Pat. No. 5,149,799 (Rubens). Conventional procedures for pregelatinizing starch are well known to those skilled in the art and described in such articles as Chapter XXII—"Production and Use of Pregelatinized Starch", Starch: Chemistry and Technology, Vol. III—Industrial Aspects, R. L. Whistler and E. F. Paschall, Editors, Academic Press, New York 1967.

The starches may also be converted to produce, inter alia, fluidity or thin-boiling starches prepared by oxidation, enzyme conversion particularly by α-amylase, acid hydrolysis, or heat and or acid dextrinization.

The present starches may be purified by any method known in the art to remove off-flavors and colors that are native to the starch or created during starch modification processes.

One skilled in the art is capable of using any single or combination of modifications in order to obtain the desired starch properties and functionality. These methods are well known in the art and the resulting starch properties and functionality will vary depending, inter alia, on the type of modification employed, the degree of modification, and the reaction conditions.

Functionality obtainable using the amylopectin cassava starches of the present invention includes without limitation encapsulation and emulsification, thickening and viscosifying, gelling, and film-forming.

The amylopectin cassava starches of the present invention may be used in a variety of industrial applications, including without limitation paper products, food products, pharmaceutical and nutritional products, personal care products and other industrial products.

Paper products is intended to include, without limitation, paper, paperboard, linerboard, corrugating, cardboard, bags, and envelopes.

Food products is intended to mean any edible product and includes, without limitation, cereals, breads and bread products, cheese and imitation cheese products, condiments, confectioneries, dressings including pourable dressings and spoonable dressings, pie fillings including fruit and cream fillings, sauces, including white sauces and dairy-based sauces such as cheese sauces, gravies, imitation and lite syrups, puddings, custards, yogurts, sour creams, pastas, beverages including dairy-based beverages, glazes, soups and baby food.

Pharmaceutical and nutritional products is intended to include pharmaceutical excipients, tablets including effervescent tablets, dusting starches and powders, and prebiotics products.

Personal care products is intended to include without limitation deodorants and antiperspirants, hair fixatives including sprays, gels, mousses, lotions and pomades, soaps and cleansers, makeup including eye shadow, powders, foundations, and blushers, shampoos and conditioners, and mouthwashes, breath fresheners and toothpastes.

Other industrial products is intended to include without limitation detergents, and biodegradable foamed products including loosefill, sheets and shapes.

The amylopectin tapioca starch may generally be used at any desired level, the amount being dependent upon the functionality to be obtained. In general, the amylopectin cassava starch will be used in an amount of from about 1% to about 95%, particularly from about 5% to about 60%, more particularly in an amount of about 10% to about 40% by weight of the product.

EXAMPLES

The following examples are presented to further illustrate and explain the present invention and should not be taken as limiting in any regard. All percents used are on a weight/weight basis.

In the examples below, the tapioca samples used are as follows:
Cassava 1=regular cassava starch grown in Thailand commercially available from National Starch and Chemical Company (Bridgewater, N.J., USA).
Cassava 2=regular cassava starch grown in Indonesia commercially available from Avebe B. A. (Foxhol, The Netherlands).
ACS 1–3=amylopectin cassava starches genetically produced by introducing the GBSS gene in the antisense mode and using FEC from which cassava plants are regenerated.
Potato=regular potato starch commercially available from Avebe B. A. (Foxhol, The Netherlands).
AMF Potato=low amylose potato starches commercially available from Avebe B. A. (Foxhol, The Netherlands).
Corn=regular corn starch commercially available from commercially available from National Starch and Chemical Company (Bridgewater, N.J., USA).
Waxy=waxy (low amylose) corn starch commercially available from National Starch and Chemical Company (Bridgewater, N.J., USA).

Example 1

Amylose Content a. Amylose content was determined by potentiometric titration. Approximately 0.5 g of a starch sample was heated in 10 mls of concentrated calcium chloride (about 30% by weight) to 95° C. for 30 minutes. The sample was cooled to room temperature, diluted with 5 mls of a 2.5% uranyl acetate solution, mixed well, and centrifuged for 5 minutes at 2000 rpm. The sample was then filtered to give a clear solution.

The starch concentration was determined polarimetrically using a 1 cm polarimetric cell. An aliquot of the sample (normally 5 mls) was then directly titrated with a standardized 0.01 N iodine solution while recording the potential using a platinum electrode with a KCl reference electrode. The amount of iodine needed to reach the inflection point was measured directly as bound iodine. The amount of amylose was calculated by assuming 1.0 gram of amylose will bind with 200 miligrams of iodine.

The results of the potentiometric titration are showed in Table 9.

TABLE 9

| Base starch | Amylose Content (%) |
|---|---|
| Cassava 1 | 20% |
| Cassava 2 | 17.4% |
| ACS 1 | 2.0% |
| ACS 2 | 2.8% |
| ACS 3 | 2.7% |

Figure 2:
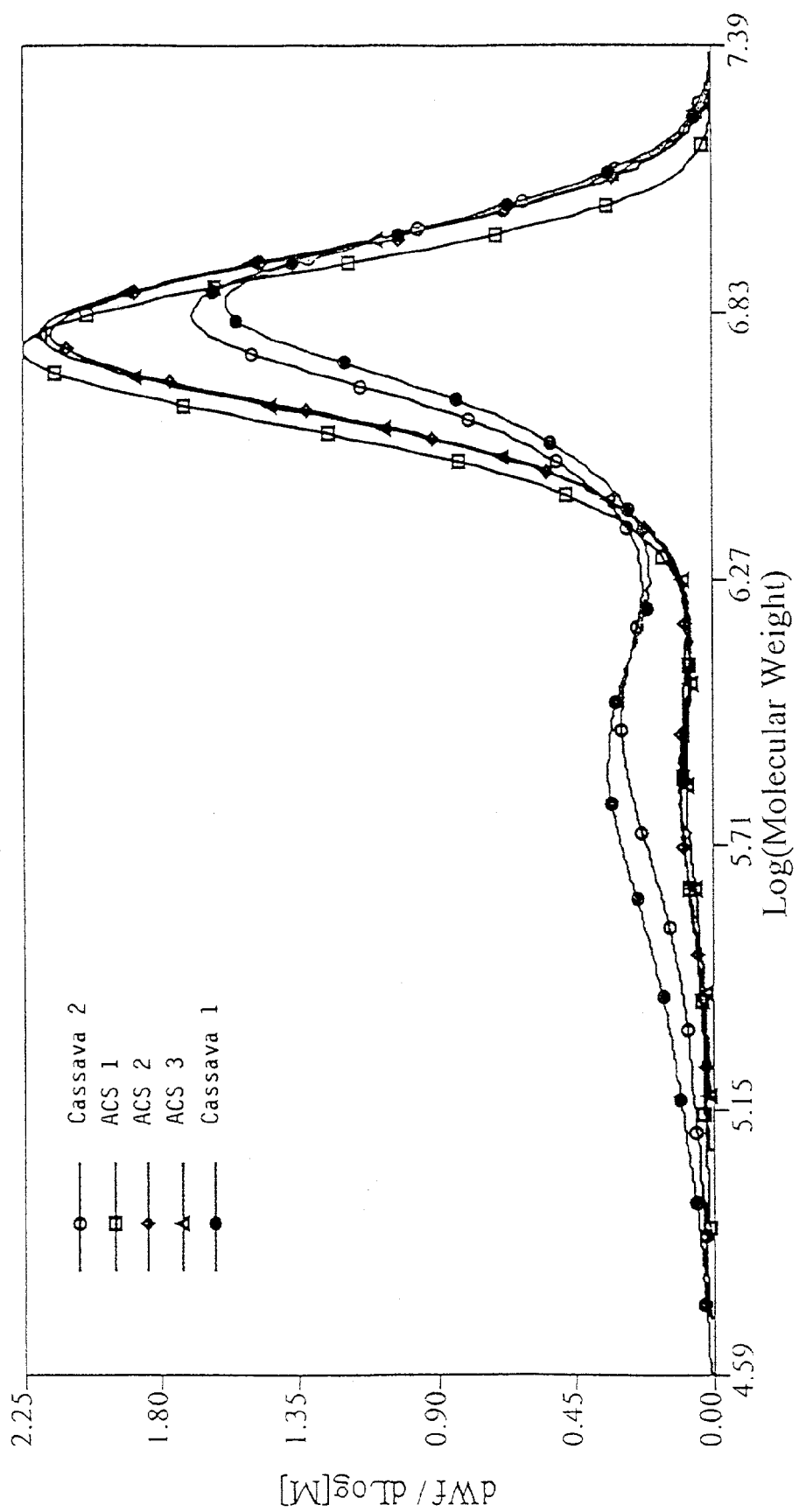
FIG. 2: Molecular weight distribution by GPC of the regular and amylopectin tapioca starches.

As can be determined from Table 9, the amylopectin cassava starches contain significantly less amylose than the regular cassava starches.

b. The amylose contents were checked by gel permeation chromatograph (GPC). Samples were prepared for analysis by slurrying 4 to 8 mg of starch in 4 g of dimethylsulfoxide (DMSO) containing 5 mM sodium nitrate and heating to 100° C. for 2 hours. The sample was filtered if necessary, and injected (300 µl) into a GPC 150C chromatograph (Waters Corporation, Amherst, Mass.). The Gel Permeation Chromatograph utilized 4 columns (guard column, $10^5$, $10^3$, $10^2$ micron (nominal) pore size columns, all from Polymer Laboratories, Amherst, Mass.). The mobile phase was dimethyl sulfoxide containing 5 mM of sodium nitrate. The instrument was operated at a temperature of 80° C. and a flow rate of 0.7 ml/minute was used. The columns were calibrated with pullulan standards (Showa Denko K. K., Japan) ranging in molecular weight from 5800 to 850,000. FIG. 2 shows the relative molecular weight distribution by GPC of the regular and amylopectin cassava starches. As can be determined from the figure, the three amylopectin cassava starches have significantly more amylopectin as seen by the peak at a relative log (molecular weight) of about 6.83. Further, this is the sole main peak. In contrast, the regular starches each show an additional amylose peak at a relative log (molecular weight of about 6.

Example 2

Structure

Debranching was accomplished by the following procedure in this example. 20 mg of starch was added to 2 ml of 90% DMSO (10% water) and stirred (at 95° C.) until dissolved. 7.980 ml of mM Acetate Buffer pH 4.8 was added to the vial and stirred. If it appeared that some of the amylose precipitated out of solution, the solution was briefly boiled until clear. Once the sample had been completely dissolved, 20 ul of pure isoamylase was added. The vial was incubated in a constant temperature bath for 16 hrs at 38° C. Upon completion, 1 ml of sample was pipetted into a 2 ml vial for chain length distribution evaluation. The remainder of the sample was precipitated in 50 ml of acetone. The precipitated material was collected by filtering using a 0.2 micron nylon filter paper and prepared for GPC.

Figure 3:
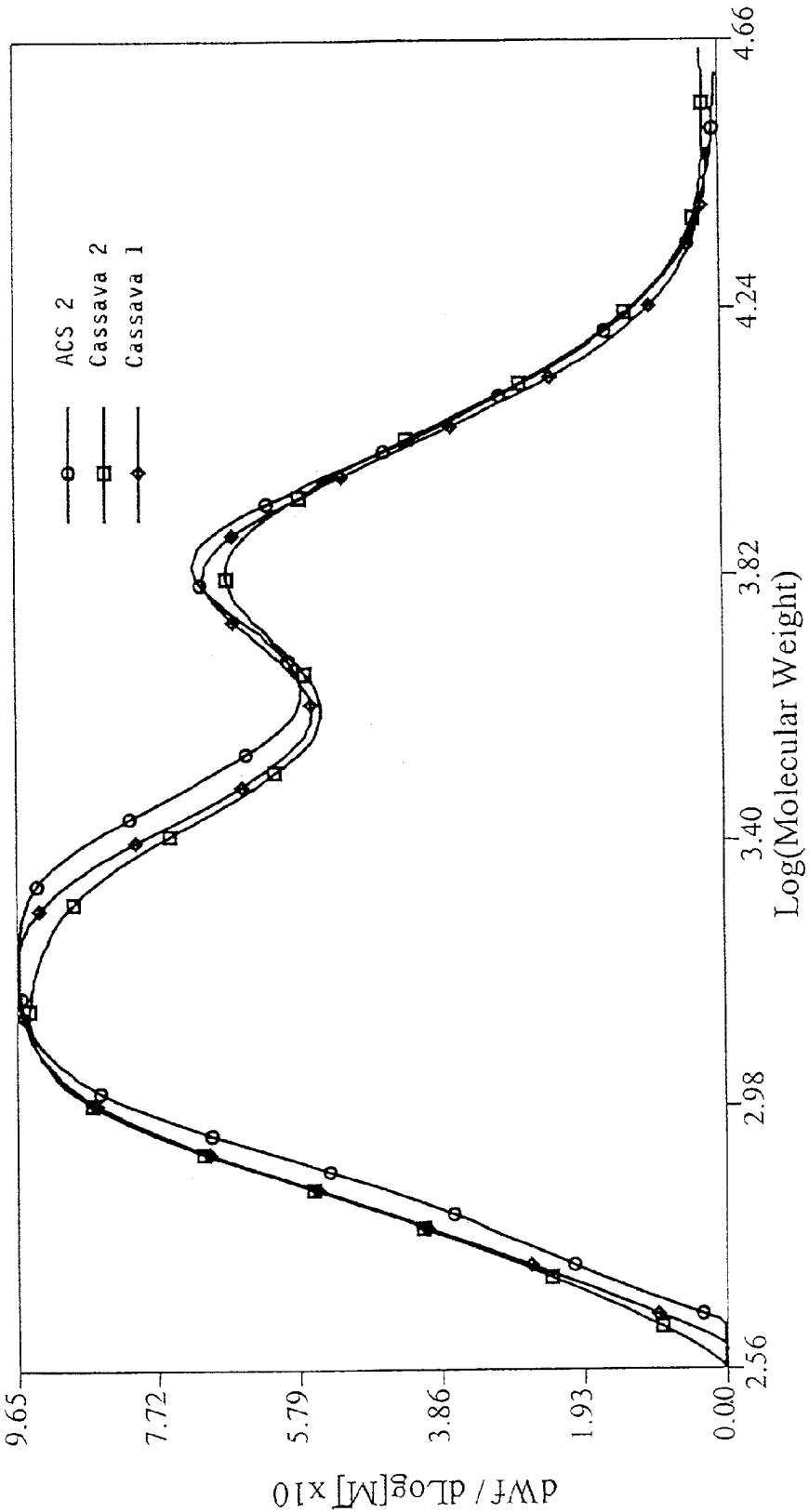
FIG. 3: Molecular weight distribution by GPC of the debranched amylopectin present in regular and amylopectin tapioca starches.
Figure 4:
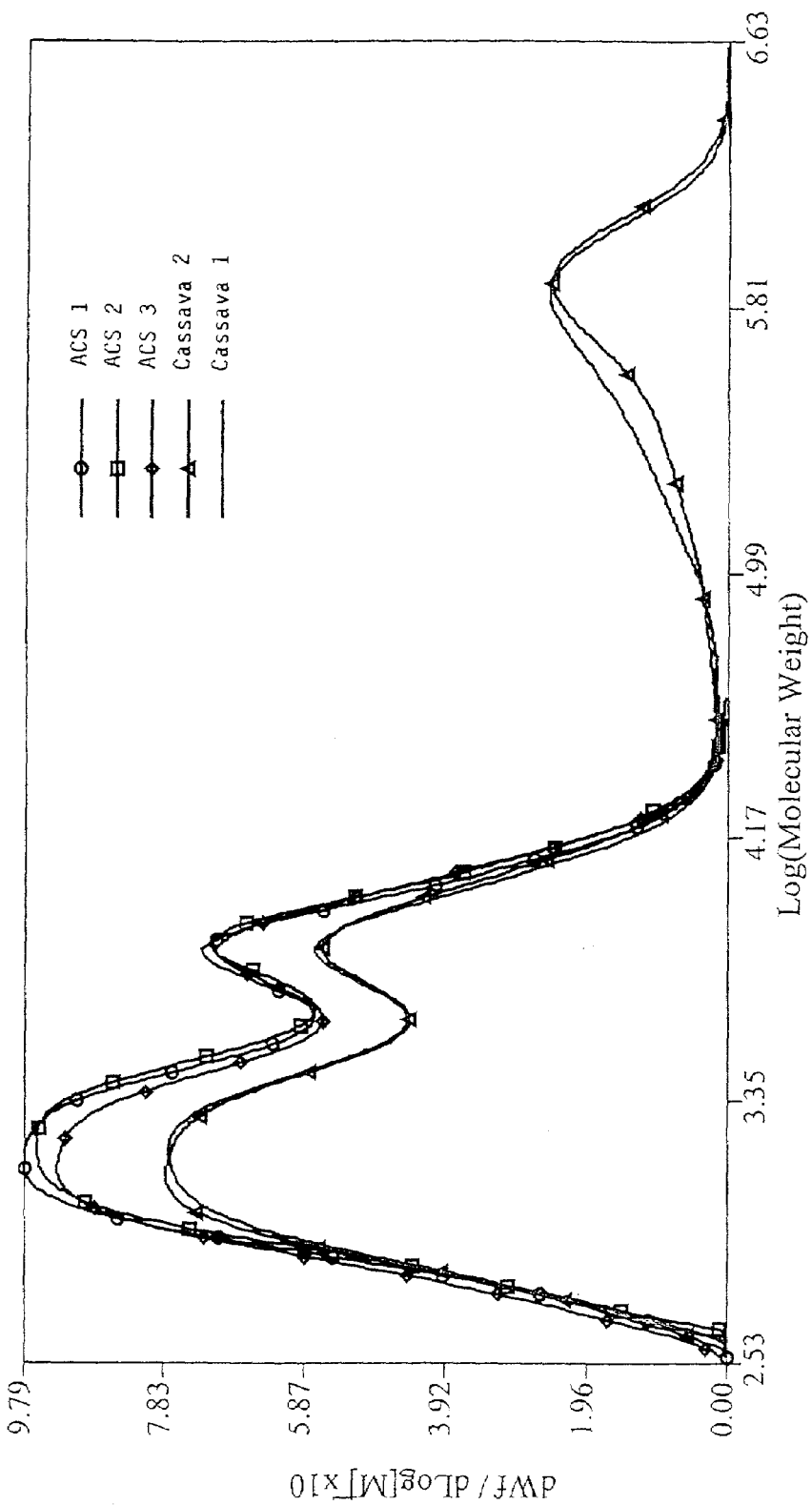
FIG. 4: Molecular weight distribution by GPC of debranched regular and amylopectin tapioca starches.

Ideally, section b should come before a. The structure of the debranched amylopectin (a) is obtained by taking the overall debranched starch chromatogram (b), and then integrating only the amylopectin peak a. The molecular weight distribution of debranched amylopectin of high amylose and regular tapioca starches were determined using GPC as in Example 1b. FIG. 3 shows the resultant molecular weight distribution of the debranched amylopectin of cassava starches. As can be seen, the amylopectin structure is substantially the same for the different cassava starches.

b. The molecular weight distribution of debranched amylopectin and regular cassava starches were determined as in a, above. FIG. 4 shows the resultant molecular weight distribution of the cassava starches. This figure confirms that the amylopectin structure is similar, but present in high quantities by substantially the same (relative) log (molecular weight) peaks at about 3.0 and 4.0. Further, this figure shows no substantial amount of amylose in the amylopectin cassava starches as evidenced by the lack of a (relative) log (molecular weight) peak at about 5.81.

Example 3

Viscosity a. Viscosity was measured using an RVA Series 4 Rapid Visco Analyzer (Newport Scientific, New South Wales, Australia). A slurry containing 5% starch on a dry weight basis was prepared and heated from 50° C. to 95° C. at a rate of 3.0° C. per minute. The sample was then held at 95° C. for five (5) minutes. Finally, the sample was cooled to 35° C. at 6.0° C. per minute. The viscosity measurements were taken at 160 rpm and the results (peak viscosity) are shown in Table 10 below.

TABLE 10

| Base starch | Viscosity (RVA Units) |
| --- | --- |
| Cassava 1 | 600 |
| Cassava 2 | 1015 |
| ACS 1 | 1230 |
| ACS 2 | 1360 |
| ACS 3 | 1330 |

Figure 5:
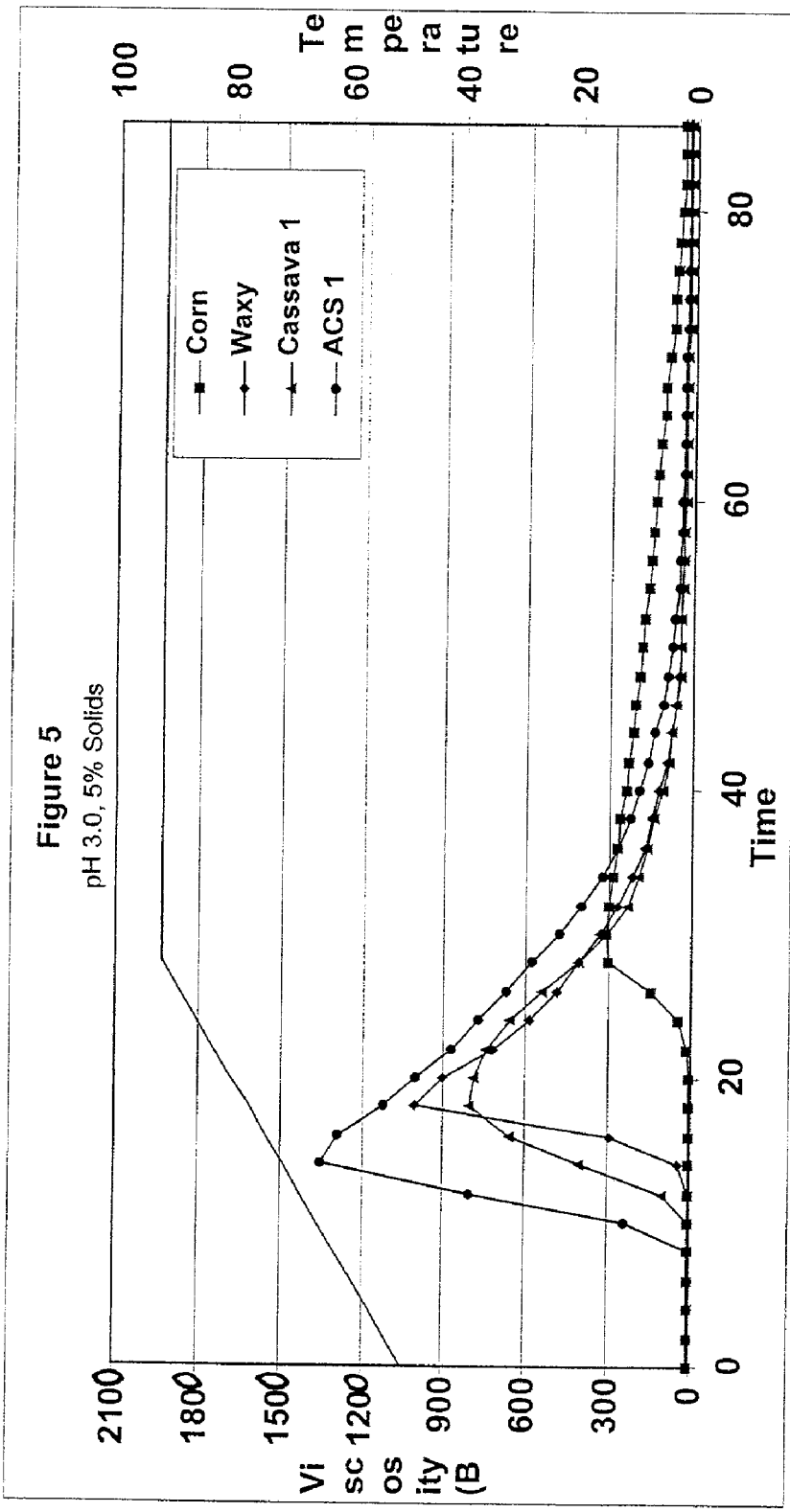
FIG. 5: Brabender viscosity of regular and amylopectin tapioca starches.

As can be seen from Table 10, the amylopectin cassava starches have significantly higher peak viscosities, about 30% more than that of the Indonesian regular cassava starch and about twice that of the Thai regular cassava starch.

b. Viscosity was also measured using a Visco/amylo/graph, Model VA-1A (C. W. Brabender Instrument Co., Hackensack, N.J., USA 07606). A slurry of 5% starch on a dry weight basis was prepared and controlled to pH3 using a citric acid/trisodium citrate buffer solution. The total charge weight of 460 grams was heated from 50° C. to 92° C. at a rate of 1.5° C. per minute. The slurry was then held at 92° C. for 30 minutes. The hot viscosity was measured while heating the paste in the Visco/amylo/graph and the resulting viscosity profile is shown in FIG. 5. This figure confirms that the amylopectin cassava starches have higher peak viscosities than those of the regular cassava starches.

Example 4

Gelatinization Temperatures a. Gelatinization temperatures were measured using differential scanning calorimetry. The starch sample is scanned from 5° C. to 140° C. at a heating rate of 10° C./min with water: starch ratio of 2:1. Duplicate runs are taken and the average is reported. The results are shown in Table 11.

TABLE 11

| Base | Onset (° C.) | Peak (° C.) | End (° C.) | (ΔH (J/g) |
| --- | --- | --- | --- | --- |
| Cassava 1 | 62.6 ± 0.4 | 69.0 ± 0.3 | 81.0 ± 0.1 | 16.05 ± 1.00 |
| Cassava 2 | 56.7 ± 0.1 | 63.2 ± 0.2 | 72.9 ± 0.3 | 16.01 ± 0.43 |
| ACS 1 | 58.1 ± 0.1 | 65.7 ± 0.0 | 74.5 ± 0.0 | 17.80 ± 0.80 |
| ACS 2 | 58.6 ± 0.0 | 65.5 ± 0.2 | 75.6 ± 0.3 | 18.08 ± 0.36 |
| ACS 3 | 58.6 ± 0.0 | 65.4 ± 0.0 | 74.5 ± 0.1 | 17.71 ± 0.20 |

As shown in Table 11, all three amylopectin cassava starches have a slightly higher onset gelatinization temperature than the Thai regular cassava starch, slightly lower than the Indonesian regular cassava starch. All three amylopectin cassava starches have a higher gelatinization enthalpy than the regular cassava starches.

b. Onset gelatinization temperatures were also checked by Brabender using the methodology of Example 3b. As can be seen from FIG. 5, the onset gelatinization temperature of the amylopectin cassava starches is lower than the regular Thai cassava.

CITED LITERATURE

Anonymus, 1985. CIAT: Annual report: Centro International de Agricultura Tropical, Cali, Columbia. Pp: 197–217.

Anthony, P., Davey, M R., Power, J. B, and Lowe, K. C. 1995. An improved protocol for the culture of cassava leaf protoplasts. Plant Cell Tissue and Organ Culture. 42:229–302

Buiteveld, J., and Creemers-Molenaar, J. 1994. Plant regeneration from protoplasts isolated. from suspension cultures of leek (*Allium ampeloprasum* L.). Plant Science. 100:203–210.

Cao, J., Duan, X., McElroy, D., and Wu, R. 1990. Regeneration of herbicide resistant transgenic rice plants following microprojectile-mediated transformation of suspension culture cells. Plant Cell Rep. 11: 586–591.

Chang, Y. F., Wang, W. C., Colleen, Y. W., Nguyen, H. T., and Wong, J R. 1991. Plant regeneration from protoplasts isolated from long-term cell cultures of wheat (*Trilicum aestivum*). Plant Cell Rep. 9:611–614.

Chen, W. H., Davey, M R., Power, J. B., and Cocking, E. C. 1988. Sugarcane protoplasts: factors affecting division and plant regeneration. Plant Cell Rep. 7:344–347.

Chen, W. H., Gartland, K. M. A., Davey, M R., Sotak, R., Gartland, J. S., Mulligan, B. J., Power, J. B., and Cocking, E. C. 1987. Transformation of sugarcane protoplasts by direct uptake of a selectable chimeric gene. Plant Cell Rep. 6:297–301.

DeLaat, A., and Blaas, J., 1987. An improved method for protoplast microinjection suitable for transfer of entire plant chromosomes. Plant Sci 50:161–169.

Fitch, M. M. M., Pang, S. Z., Slightom, Lius. S., Tennant, P., Manshardt, R. M., and Gonsalves, D. 1994. Genetic transformation in *Carica papaya* (Papaya). In: Bajai (Eds). Biotechnology in Agriculture and Forestry Vol. 29. Plant protoplasts and genetic engineering V. Springer-Verlag, Berlin. P:237–255.

Dons, J. J. M., and Bouwer, R. 1986. Improving the culture of cucumber protoplasts by using an agarose-disc procedure. Proceedings of an international symposium on nuclear techniques and in vitro culture for plant improvement. Jointly organized by the International Atomic Energy Agency and the Food and Agriculture Organization of the United Nations. Held in Vienna, 19–23, Aug. 1985. P:498–504.

Fraley R. T., Rogers S. G., and Horsch, R. B. 1986. Genetic transformation in higher plants. CRC Critical reviews in Plant Sciences 4(1):1–46.

Gordon-Kamm, W. J., Spencer, T M, Mangano, M. R., Adams, T. R., Daines, R. J., William, G. S., OBrien, J. V., Chambers, S. A. Adams, Jr. W. R., Willetts, N. G., Rice, T. B., Mackey C. J., Krueger, R. G., Kausch, A. P. and Lemaux P. G. 1990. Transformation of maize cells and regeneration of fertile transgenic plants. The Plant Cell. 2:603–618.

Gresshoff, P. M., and Doy, C. H. 1974. Development and differentiation of haploid *Lycopersicon esculentum* (tomato). Planta 107:161–170.

Griesbach, R. J., and Hammond, J. 1993. Incorporation of the GUS gene into orchids via embryo electrophoresis. Acta. Hort. 336:165–169.

Guerineau F. & Mullineaux P. M. 1993. Plant transformation and expression vectors. In: Croy R. R. D. (ed.), Plant Mol. Biol. Labfax, BIO.S Scientific publishers, Oxford, UK. 1993, pp. 121–148

Horn, M. E., Shillito, R. D., Conger, B. V., and Harms, C. T. 1988. Transgenic plants of, orchardgrass (*Dactylis glomerata L.*) from protoplasts. Plant Cell Rep. 7:469–472.

Hovenkamp-Hermelink, J H M, De Vries J N, Admase P, Jacobsen E, Withold B, Feenstra W J, 1988. Rapid estimation of the amylose/amylopectin ration in small amounts of tuber and leaf tissue of potato. Potato Res. 31: 241–246.

Jones H., Tempelaar M. J., and Jones, M. G. K. 1987. Recent advances in plant electroporation. Oxford Surveys of Plant Mol. and Cell Biol. 4:347–357.

Kaeppler, H. F., Gu, W., Somres, D. A., Rines, H. W., Cockburn, A. F. 1990. Silicon carbide fiber-mediated DNA delivery into plant cells. Plant Cell Rep. 8:415–418.

Klein T. M., Kornstein L., Sanfords J. C., and Fromm M E. 1989. Genetic transformation of maize cells by particle bombardment. Plant Physiol. 91:440–444.

Konan N. K., Sangwan R. S., and Sangwan-Norren. 1994. Nodal axillary meristems as target tissue for shoot production and genetic transformation in cassava (*Manihot esculenta* Crantz). Second International Scientific Meeting of Cassava Biotechnology Network 11. Bogor. Indonesia. p:276–288.

Kyozuka, J., Otoo; E., and Shimamoto, K. 1988. Plant regeneration from protoplasts of indica rice: genotypic differences in culture respond. Theor. Appl. Genet. 76:887–890.

Lörz, H., Baker, B., and Schell, J. 1985. Gene transfer to cereal cells mediated by protoplast transformation. Mol. Gen. Genetic 199: 178–182.

Luong, H. T., Shewry, P. R., and Lazzeri, P. A. 1994. Gene transfer to cassava somatic embryos via tissue electroporation and particle bombardment. In: Second International Scientific Meeting of Cassava Biotechnology Network 11. Bogor. Indonesia. p:303–314.

Mathews, H., Carcamo, R., Chavarriaga, Schöpke, C. P., Fauquet, C. and Beachy, R. N., 1993. Improvement of somatic embryogenesis and plant recovery in cassava. Plant Cell Rep. 12:328–333.

Mroginski and Scocchi, 1992. Somatic embryogenesis of Argentine cassava varieties. In: Roca, W. M., and Thro, A. M. (Eds). Proceedings First Scientific Meeting of the Cassava Biotechnolgy Network. Cartagena, Colombia 25–28, Aug. 1985. P: 175–179.

Mukherjee, A. 1994. Embryogenesis and regeneration from cassava Galli of anther and leaf. The Cassava Biotechnology Network. Proceeding of the Second International Scientific Meeting. Bogor, Indonesia, 22–26, Aug. 1985 P:375–377, Murashige, T., and Skoog, F. 1962 A revised medium for rapid growth and bioassay with tobacco cultures. Physiol. Plantarum 15 473–497.

Nakano, M., Hoshino, Y., and Mil, M. 1994. Regeneration of transgenic plants of grapevine (*Vitis Vinifera L.*) via *Agrobacterium* rhizogenesis-mediated transformation of embryogenic calli. J. of Exp. Bot. 45 (274):649–656.

Narayanaswamy, T. C., Ramaswamy, N. M., and Sree Rangaswamy, S R. 1995. Somatic embryogenesis and plant regeneration in cassava. The Cassava Biotechnology Network. Proceeding of the Second International Scientific Meeting. Bogor, Indonesia, 22–26, Aug. 1985. P:324–329.

Ng S Y C (1992) Tissue culture of root and tuber crops at IITA. In: Thottappilly G, Monti L M, Mohan Raj D R, Moore A W (eds), Biotechnology: enhancing research on tropical crops in Africa CTA/IITA co-publication, IITA, Ibadan, Nigeria, pp 135–141.

Nzoghe, D. 1989. Recherche de conditions permettant l'obtention neoformations chez differents genotypes de manioc (*Manihot esculenta* Crantz). Extension a la culture de protoplastes. These. Universite De Paris Sud Centre D'Orsay. P: 119.

Ow, D. W., Wood, K. V., DeLuca, M., De Wet, J R., Helinski, D R., and Howell, S. H. 1986. Transient and stable expression of the firefly luciferase gene in plant cells and transgenic plants. Science 234:856–859.

Potrykus, I, Saul, M., Paskowski, J., and Shillito, R. D. 1985. Direct gene transfer into protoplasts of a graminacious monocot. Mol. Gen. Genet. 199:183–188.

Power, J. B., Bery, S. F., Chapman J. V., and Cocking, E. C. 1979. Somatic hybrids between unilateral cross-incompatible *Petunia* species. Theor. Appl. Genet. 55: 97–99.

Raemakers, C. J. J. M. 1993. Primary and cyclic somatic embryogenesis in cassava *Manihot esculenta* Crantz. PhD thesis Agricultural University Wageningen, The Netherlands. P:119.

Raemakers, C. J. J. M., Bessembinder, J., Staritsky, G., Jacobsen, E., and Visser, R. G. F. 1993a. Induction, germination and shoot development of somatic embryos in cassava. Plant Cell Tissue and Organ Culture 33:151–156.

Raemakers, C. J. J. M., Amati, M., Staritsky, G., Jacobsen, E., and Visser, R. G. F. 1993b. Cyclic somatic embryogenesis and plant regeneration in cassava. Annals of Bot. 71:289–294.

Raemakers, C. J. J. M., Schavemaker, C. M., Jacobsen, E., and Visser, R. G. F. 1993c. Improvements of cyclic somatic embryogenesis of cassava (*Manihot esculenta* Crantz). Plant Cell Rep. 12:226–229.

Raemakers K, Schreuder, M, Muniykwa, T., Jacobsen E. and & Visser R., 2000. Towards a routine transformation procedure for cassava. In: Carvalho, L. J. C. B., Thro, A.

M. and Vilarinhos A. D. (eds). Cassava biotechnology IV international scientific meeting-CBN, pp. 250–267. (ISBN85-87697-05-6). Brazilian Agricultural Research Cooperation-EMBRAPA, Brazil.

Raemakers K, Schreuder, M, Pereira, I., Muniykwa, T., Jacobsen E. and & Visser R., 2001. Progress made in FEC transfformation of cassava. Euphytica (in press)

Rhodes, C. A., Pierce, D. A., Metler, I. J., Mascarenhas, D., and Detmer, J. J. 1988. Genetically transformed maize plants Erom protoplasts. Science 240:204–207.

Salehuzzaman S. N. I. M., Jacobsen, E and RGF Visser, 1993. Isolation and characterisation of a cDNA encoding granula-bound starch synthase from cassava ((*Manihot esculenta* Crantz) and its antisense expression in potato. Plant Molecular Biology 23:947–962.

Salehuzzaman S. N. I. M., Jacobsen, E and RGF Visser, 1994. Expression patterns of two starch biosynthetic genes in in vitro cultured cassava plants and their induction by Plant Science 98:53–62.

Schenk R. U. & Hildebrandt A. C. 1972. Medium and techniques for induction and growth of monocotyledonous and dicotyledonous plant cell cultures. Canadian Journal of Botany 50:199–204.

Schreuder, M. M., Raemakers C. J. J. M., Jacobsen E. & Visser R. G. F. 2001. Efficient production of transgenic plants by *Agrobacterium*-mediated transformation of cassava (*Manihot esculenta* Crantz.). Euphytica (in press).

Scorza, R., Cordts, J. M., Ramming, D. W., and Emershad, R. L. 1995. Transformation of grape (*Vitis vinifera L.*) zygotic-derived somatic embryos and regeneration of transgenic plants. Plant Cell Rep 14:589–592.

Shahin, E. A., and Shepard, J. F. 1980. Cassava mesophyll protoplasts: isolation, proliferation and shoot formation. Plant Science Letters 17:459–465.

Shimamoto, K., Terada, R., Izawa, T., and Fujimoto, H. 1989. Fertile transgenic rite plants regenerated from transformed protoplasts. Nature 338:274–276.

Sofiari, E, 1996. Regenration and transfonmation in cassava *Manihot esculenta* Crantz. PhD thesis Agricultural University Wageningen, The Netherlands. P: 136.

Songstad, D. D., Somers, D. A., and Griesbach, R. J. 1995. Advances in alternative DNA delivery techniques. Plant Cell Tissue and Organ Culture 40: 1–15.

Stamp, J. A., and Henshaw, G. G. 1987a. Somatic embryogenesis from clonal leaf tissue of cassava. Annals of Bot. 59:445–450.

Stamp, J. A. 1987. Somatic embryogenesis in cassava: the anatomy and morphology of the regeneration process. Annals of Bot. 59: 451–459. Stamp, J. A., and Henshaw, G. G. 1987b. Secondary somatic embryogenesis and plant regeneration in cassava. Plant Cell Tissue and Organ Culture 10:227–233;

Stamp, J. A., and Henshaw, G. G. 1982. Somatic embryogenesis in cassava. Zeitschrift für Pflanzenphysiologie. 105:183–187.

Sudarmonowati and Bachtiar, 1995. Induction of somatic embryogenesis in Indonesian cassava genotypes. The Cassava Biotechnology Network. Proceeding of the Second International Scientific Meeting. Bogor, Indonesia, Aug. 22–26, 1994. P:364–374).

Sudarmonowati. E., and G. G. Henshaw. 1992. The induction of somatic embryogenesis of recalcitrant cultivars using picloram and dicamba. In: Roca, W. M., and Thro, A. M. (Eds). Proceedings First Scientific Meeting of the Cassava Biotechnology Network. Cartagena, Colombia 25–28, Aug. 1985. P: 128–133.

Suhandano, S., Hughes, J., Brown, K., Sirju-Charan, G., Hughes, M., 2000. Characterization of an elongation factor-1-alpha gene from cassava (*Manihot esculenta* Crantz): a new promoter for biotechnology. In: Carvalho, L. J. C. B., Thro, A. M. and Vilarinhos A. D. (eds). Cassava biotechnology IV international scientific meeting-CBN, pp. 572–581. (ISBN85-87697-05-6). Brazilian Agricultural Research Cooperation-EMBRAPA, Brazil.

Szabados L., Hoyos R. and Roca W. 1987. In vitro somatic embryogenesis and plant regeneration of cassava. Plant Cell Rep. 6:248–251.

Taylor, N. J., Clarke, M., and Henshaw, G. G. 1992. The induction of somatic embryogenesis in fifteen African cassava cultivars. In: Roca, W. M., and Thro, A. M. (Eds). Proceedings First Scientific Meeting of the Cassava Biotechnology Network. Cartagena, Colombia 25–28, Aug. 1985. P: 134–137.

Taylor, N. J., Edwards, M., and Henshaw, G. G. 1995. Production of friable embryogenic calli and suspension culture system in two genotypes of cassava. Second International Scientific Meeting of Cassava Biotechnology Network ll. Bogor. Indonesia. P:229–240.

Taylor, N. J., Masona, M. V., Schopke C., Carcamo, R., Ho. T., Gonzalez, A. E., Beaychy, R. N. and Fauqet, C., 2000. Production of genetically modified plants containing various genes of interest. In: Carvalho, L. J. C. B., Thro, A. M. and Vilarinhos A. D. (eds). Cassava biotechnology IV international scientific meeting-CBN, pp. 267–276. (ISBN85-87697-05-6). Brazilian Agricultural Research Cooperation-EMBRAPA, Brazil.

Thompson, J. C., Movva, N. R., Tizard, R., Crameri, R., Davies, J. E., Lauwereys, M., and Botterman, J. 1987. Characterization of the herbicide-resistance gene bar from *Streptomyces hygroscopicus*. The EMBO J.6 (9):2319–2523.

Toriyama, K., Arimoto, Y., Uchimiya, H., and Hinata, K. 1988. Transgenic rice plants after direct gene transfer into protoplasts. Bio/Technology. 6:1072–1074.

Thro, A M T, Fregene, M., Raemakers C J J M, Puonti Kaerlas, J., Schopke C., Visser, R., Potrykus, I., Fauqet, C., Roca, W., Hershey, C., 1999. Genetic biotechnologies and cassava-based development. In: Hohn, T and Leisinger, K. M. (eds.). Biotechnology of food crops in developing countries. pp 141–185. SpringerWien NewYork (ISBN3-211-83240-8).

Visser R G F, Hergersberg M, van der Ley F R, Jacobsen E, Witbolt B, Feenstra W J, 1989. Molecular cloning and partial characterization of the gene for granula-bound starch synthase from a wild type and a amylose-free potato. Plant Sci 64185–192.

Visser R G F, Stolte A, Jacobsen E, 1991. Expression of a chimeric granula-bound starch synthase-GUS gene in transgenic potato tubers. Plant Physiol 82:411–416.

Walker, P. M. B. 1989. Chambers Biology Dictionary. W&R Chamber Ltd. Clay Ltd, St. Ives Plc. England. P:205.

Wolters, A. M. A., Schoenmakers, H. C. H., van der Meulen-Muiser, J. J. M., van der Knaap, E., Derks, F. H. M., Koornneef, M., and Zelcer, A. 1991. Limited DNA elimination from the irradiated potato parent in fusion products of albino *Lycopersicon esculentum* and *Solanum luberosum*. Theor. Appl. Genet. 83:225–232.

Wordragen M. F., and Dons, H I N L 1992. *Agrobacterium tumefaciens* mediated transformation of recalcitrant crops. Plant Mol. Biol. Reporter 10: 12–36.

Woodward, B., and Puonti Kaerlas, 2001. Somatic embryogenesis from floral tissues of cassava (*Manihot esculenta* Crantz. Euphytica (in press).

We claim:

1. A starch obtainable by isolating starch from a tuber of a cassava plant obtainable by regenerating plants from protoplasts wherein the protoplast is induced to produce an embryo, which embryo is consequently induced to produce a plant;
   wherein the protoplast is produced by the method which comprises producing friable embryogenic callus from explants of cassava and isolating protoplasts from said friable embryogenic callus;
   wherein the isolation comprises the steps of:
      washing the tuber, followed by grating and milling it;
      separating starch from fibers and juice in a separator;
      sieving the starch;
      washing the starch; and
      drying the starch,
   said starch having an amylopectin content of at least 95 wt. % based on the (dry substance) weight of the starch.

2. The starch of claim 1 having an amylopectin content of at least 98 wt.%, based on the (dry substance) weight of the starch.

3. A native amylopectin cassava starch.

4. The starch of claim 3, wherein the starch has an amylopectin content of at least about 90% by weight.

5. The starch of claim 3, wherein the starch has an amylopectin content of at least about 95% by weight.

6. The starch of claim 3, wherein the starch has an amylopectin content of at least about 98% by weight.

7. The starch of claim 3, wherein the viscosity of the starch is at least about 30% greater than that of regular cassava starch.

8. The starch of claim 3, wherein the viscosity of the starch is at least about 50% greater than that of regular cassava starch.

9. The starch of claim 3, wherein the viscosity of the starch is at least about 80% greater than that of regular cassava starch.

10. The starch of claim 3, which has been modified physically by thermal inhibition or shear, modified chemically to form ethers, esters, half esters, acetates, phosphates, succinates, tertiary amine ethers, or quaternary amine ethers, or modified enzymatically by alpha-amylase, beta-amylase, glucoamylase, maltogenic alpha-amylase, isoamylase, or pullulanase.

* * * * *